US011071449B2

(12) United States Patent
Heeren

(10) Patent No.: US 11,071,449 B2
(45) Date of Patent: Jul. 27, 2021

(54) VISUALIZATION SYSTEM FOR OPHTHALMIC SURGERY

(71) Applicant: Alcon Inc., Fribourg (CH)

(72) Inventor: Tammo Heeren, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 992 days.

(21) Appl. No.: 15/087,585

(22) Filed: Mar. 31, 2016

(65) Prior Publication Data

US 2017/0280989 A1 Oct. 5, 2017

(51) Int. Cl.
| | | |
|---|---|---|
| A61B 3/00 | (2006.01) |
| A61B 3/10 | (2006.01) |
| A61B 3/13 | (2006.01) |
| A61B 3/14 | (2006.01) |
| A61B 5/06 | (2006.01) |
| A61B 5/00 | (2006.01) |

(Continued)

(52) U.S. Cl.
CPC .......... *A61B 3/0025* (2013.01); *A61B 3/0058* (2013.01); *A61B 3/10* (2013.01); *A61B 3/102* (2013.01); *A61B 3/1005* (2013.01); *A61B 3/1025* (2013.01); *A61B 3/13* (2013.01); *A61B 3/14* (2013.01); *A61B 5/0066* (2013.01); *A61B 5/065* (2013.01); *A61B 5/066* (2013.01); *A61B 5/684* (2013.01); *A61B 5/6844* (2013.01); *A61B 34/20* (2016.02); *G02B 21/0012* (2013.01); *G02B 21/22* (2013.01); *G02B 21/365* (2013.01);

(Continued)

(58) Field of Classification Search
CPC ...... A61B 2034/2065; A61B 2090/306; A61B 2090/3735; A61B 2090/365; A61B 2505/05; A61B 3/102; A61B 2017/00115; A61B 2017/00119; A61B 2034/2048; A61B 34/20; G01B 9/02091

See application file for complete search history.

(56) References Cited

U.S. PATENT DOCUMENTS

| | | |
|---|---|---|
| 8,265,364 B2 | 9/2012 | Raksi |
| 9,412,161 B2 | 8/2016 | Varaklis et al. |

(Continued)

FOREIGN PATENT DOCUMENTS

| | | |
|---|---|---|
| CN | 103156573 A | 6/2013 |
| CN | 104334072 A | 2/2015 |

(Continued)

*Primary Examiner* — Baisakhi Roy

(57) ABSTRACT

An ophthalmic surgical system includes an imaging unit configured to generate a fundus image of an eye and a depth imaging system configured to generate a depth-resolved image of the eye. The system further includes a tracking system communicatively coupled to the imaging unit and depth imaging system, the tracking system comprising a processor and memory configured to analyze the fundus image generated by the imaging unit to determine a location of a distal tip of a surgical instrument in the fundus image, analyze the depth-resolved image generated by the depth imaging system to determine a distance between the distal tip of the surgical instrument and a retina of the eye, generate a visual indicator to overlay a portion of the fundus image, the visual indicator indicating the determined distance between the distal tip and the retina, modify the visual indicator to track a change in the location of the distal tip within the fundus image in real-time, and modify the visual indicator to indicate a change in the distance between the distal tip of the surgical instrument and the retina in real-time.

19 Claims, 17 Drawing Sheets

(51) Int. Cl.
  *G02B 21/36* (2006.01)
  *A61B 34/20* (2016.01)
  *G02B 21/00* (2006.01)
  *G02B 21/22* (2006.01)
  *A61B 90/00* (2016.01)
  *A61F 9/007* (2006.01)
  *A61B 90/30* (2016.01)

(52) U.S. Cl.
  CPC . *A61B 2034/2065* (2016.02); *A61B 2090/306* (2016.02); *A61B 2090/365* (2016.02); *A61B 2090/3735* (2016.02); *A61B 2505/05* (2013.01); *A61F 9/007* (2013.01)

(56) References Cited

U.S. PATENT DOCUMENTS

| | | | |
|---|---|---|---|
| 2009/0163898 A1* | 6/2009 | Gertner | A61B 3/113 606/4 |
| 2009/0182312 A1 | 7/2009 | Gertner et al. | |
| 2010/0168763 A1 | 7/2010 | Zhao et al. | |
| 2012/0069302 A1 | 3/2012 | Juhasz et al. | |
| 2012/0184846 A1* | 7/2012 | Izatt | G02B 21/0012 600/425 |
| 2014/0221822 A1* | 8/2014 | Ehlers | A61B 5/061 600/424 |
| 2015/0173644 A1* | 6/2015 | Ren | A61B 5/066 600/424 |
| 2016/0166336 A1* | 6/2016 | Razzaque | A61B 34/25 606/130 |
| 2016/0360959 A1 | 12/2016 | Heeren et al. | |

FOREIGN PATENT DOCUMENTS

| | | |
|---|---|---|
| JP | 2014188275 A | 10/2014 |
| KR | 20120101040 A | 9/2012 |
| WO | 2011/053921 A2 | 5/2011 |

* cited by examiner

VISUALIZATION SYSTEM FOR OPHTHALMIC SURGERY

FIELD

The present disclosure relates generally to surgical procedures, and more particularly to ophthalmic surgical visualization systems and methods.

BACKGROUND

Many microsurgical procedures require precision cutting and/or removal of body tissues. For example, certain ophthalmic surgical procedures require the cutting and/or removal of the vitreous humor, a transparent jelly-like material that fills the posterior segment of the eye. The vitreous humor, or vitreous, is composed of microscopic fibrils that are often attached to the retina. Cutting and removal of the vitreous must be done with great care to avoid traction on the retina, the separation of the retina from the choroid, a retinal tear, or, in the worst case, cutting and removal of the retina itself. Delicate operations such as mobile tissue management (e.g., cutting and removal of vitreous near a detached portion of the retina or a retinal tear), vitreous base dissection, and cutting and removal of membranes are particularly difficult.

Microsurgical cutting probes used in posterior segment ophthalmic surgery are typically inserted via an incision in the sclera near the pars plana. The surgeon may also insert other microsurgical instruments such as a fiber optic illuminator, an infusion cannula, an imaging probe (e.g., an OCT probe), or an aspiration probe during the posterior segment surgery.

To aid the surgeon with these types and other types of surgical procedures, surgeons may use an imaging system that presents a microscope view of the tissue to be treated, such as tissue of the patient's eye. Accordingly, the user of such an imaging system may be provided with a close-up view of the surgical instruments, such as forceps or other tools, as well as the region of the eye that is of interest. Such systems may also provide additional information that may be useful to the surgeon, such as an Optical Coherence Tomography (OCT) image of the region of the eye that is of interest. OCT imaging generally utilizes near-infrared light and is able to obtain or generate images of tissue beneath the surface.

Despite advances in imaging systems, performing ocular surgical procedures remains challenging. Among other things, it may be difficult for a surgeon viewing a stereo microscope image to discern with precision the depth of a surgical tool inserted in the eye and its proximity to particular tissues, such as the retina. Surgeons typically rely on experience and judgment developed over time for guidance during delicate procedures, and improved techniques for visualization are needed to improve patient safety and surgical outcomes.

SUMMARY

In certain embodiments, an ophthalmic surgical system includes an imaging unit configured to generate a fundus image of an eye and a depth imaging system configured to generate a depth-resolved image of the eye. The system further includes a tracking system communicatively coupled to the imaging unit and depth imaging system. The tracking system includes a processor and memory configured to analyze the fundus image generated by the imaging unit to determine a location of a distal tip of a surgical instrument in the fundus image, analyze the depth-resolved image generated by the depth imaging system to determine a distance between the distal tip of the surgical instrument and a retina of the eye, generate a visual indicator to overlay a portion of the fundus image, the visual indicator indicating the determined distance between the distal tip and the retina, modify the visual indicator to track a change in the location of the distal tip within the fundus image in real-time, and modify the visual indicator to indicate a change in the distance between the distal tip of the surgical instrument and the retina in real-time.

The processor and memory of the tracking system may be further configured to determine a distance between the distal tip of the surgical instrument and a retina of the eye based on an analysis of image pixels in the depth-resolved image.

The depth-imaging system may be configured to generate a depth-resolved image of the eye based on signals received by an imaging probe integrated with the surgical instrument.

In certain embodiments, the processor and memory of the tracking system are configured to generate the visual indicator to overlay the distal tip of the surgical instrument within the fundus image.

The processor and memory of the tracking system may be configured to modify the visual indicator to indicate the change in the distance between the distal tip of the surgical instrument and the retina by increasing or decreasing the size of the visual indicator in proportion to the change in distance between the distal tip of the surgical instrument and the retina.

In certain embodiments, the processor and memory of the tracking system are configured to modify the visual indicator to indicate the change in the distance between the distal tip of the surgical instrument and the retina by modifying a color of the visual indicator.

According to certain embodiments, the depth imaging system is an Optical Coherence Tomography (OCT) system configured to generate an OCT image of the eye. The OCT system may include an OCT light source operable to generate an OCT imaging beam and a beam scanner operable to direct the OCT imaging beam. The tracking system may be configured to analyze the OCT image to determine the distance between the distal tip of the surgical instrument and the retina of the eye. The processor and memory of the tracking system may be configured to cause the beam scanner to direct the OCT imaging beam to a particular region of the eye that includes the distal tip of the surgical instrument, based on the determined location of the distal tip of the surgical instrument within the fundus image.

In certain embodiments, the surgical instrument includes a first optical fiber configured to transmit the OCT imaging beam, and a second optical fiber configured to transmit light reflected by the eye.

According to certain embodiments, the processor and memory of the tracking system are configured to determine the location of the distal tip of the surgical instrument in the fundus image by generating an enhanced image of the fundus image, estimating a marker image within the enhanced image, extracting the marker image from the enhanced image, and determining a location of the marker from the image of the marker.

In certain embodiments, the visual indicator and fundus image are displayed in an eyepiece or on a heads-up screen. The visual indicator may also be configurable by a user.

In certain embodiments, the imaging unit comprises at least one of a surgical microscope, a 2-dimensional camera, a line-scan camera, and a single detector as used in a confocal scanning ophthalmoscope.

Certain embodiments include a method that includes generating a fundus image of an eye, generating a depth-resolved image of the eye, analyzing the fundus image to determine a location of a distal tip of a surgical instrument in the fundus image, analyzing the depth-resolved image to determine a distance between the distal tip of the surgical instrument and a retina of the eye, generating a visual indicator to overlay the distal tip of the surgical instrument within the fundus image, the visual indicator indicating the determined distance between the distal tip and the retina, modifying the visual indicator to track a change in the location of the distal tip within the fundus image in real-time, and modifying the visual indicator to indicate a change in the distance between the distal tip of the surgical instrument and the retina in real-time.

According to certain embodiments, modifying the visual indicator to indicate a change in the distance between the distal tip of the surgical instrument and the retina in real-time includes increasing or decreasing the size of the visual indicator in proportion to the change in distance between the distal tip of the surgical instrument and the retina.

In certain embodiments, modifying the visual indicator to indicate a change in the distance between the distal tip of the surgical instrument and the retina in real-time includes modifying a color of the visual indicator.

Certain embodiments further include directing an imaging beam of an imaging system to a particular region of the eye that includes the distal tip of the surgical instrument, based on the determined location of the distal tip of the surgical instrument within the fundus image.

In certain embodiments, analyzing the fundus image to determine a location of a distal tip of a surgical instrument in the fundus image includes generating an enhanced image of the fundus image, estimating a marker image within the enhanced image, extracting the marker image from the enhanced image, and determining a location of the marker from the image of the marker.

In certain embodiments, the method includes displaying the visual indicator in an eyepiece or on a heads-up screen. The method may also include receiving user input related to a type of visual indicator.

Certain embodiments of the present disclosure may provide one or more technical advantages. For example, certain embodiments provide a visual indicator that may allow a surgeon to perform a vitrectomy with increased precision, and reduce the risk of damaging the retina during a vitrectomy. In particular, certain embodiments provide a visual indicator displayed as an overly at the position of a distal tip of a surgical instrument. This aspect may assist a surgeon by providing accurate, real-time information about the actual and/or relative location of, and distance between, a surgical tool and sensitive tissue without obstructing the surgeon's view of surrounding tissue. Further, by providing an indicator to alert a surgeon of the precise location of a surgical instrument, including its proximity to sensitive tissue such as a retina, certain embodiments increase the surgeon's precision, awareness, and confidence, improving patient safety and surgical outcomes. Moreover, the indicator may be provided as an image overlay within an eyepiece or heads-up display so that a surgeon may easily monitor the indicator without diverting attention from the surgical field. Additionally, features or aspects of the indicator may be modified in proportion to changes in the proximity of the tool and eye tissue, thereby providing intuitive and immediate feedback to the surgeon regarding tool position.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
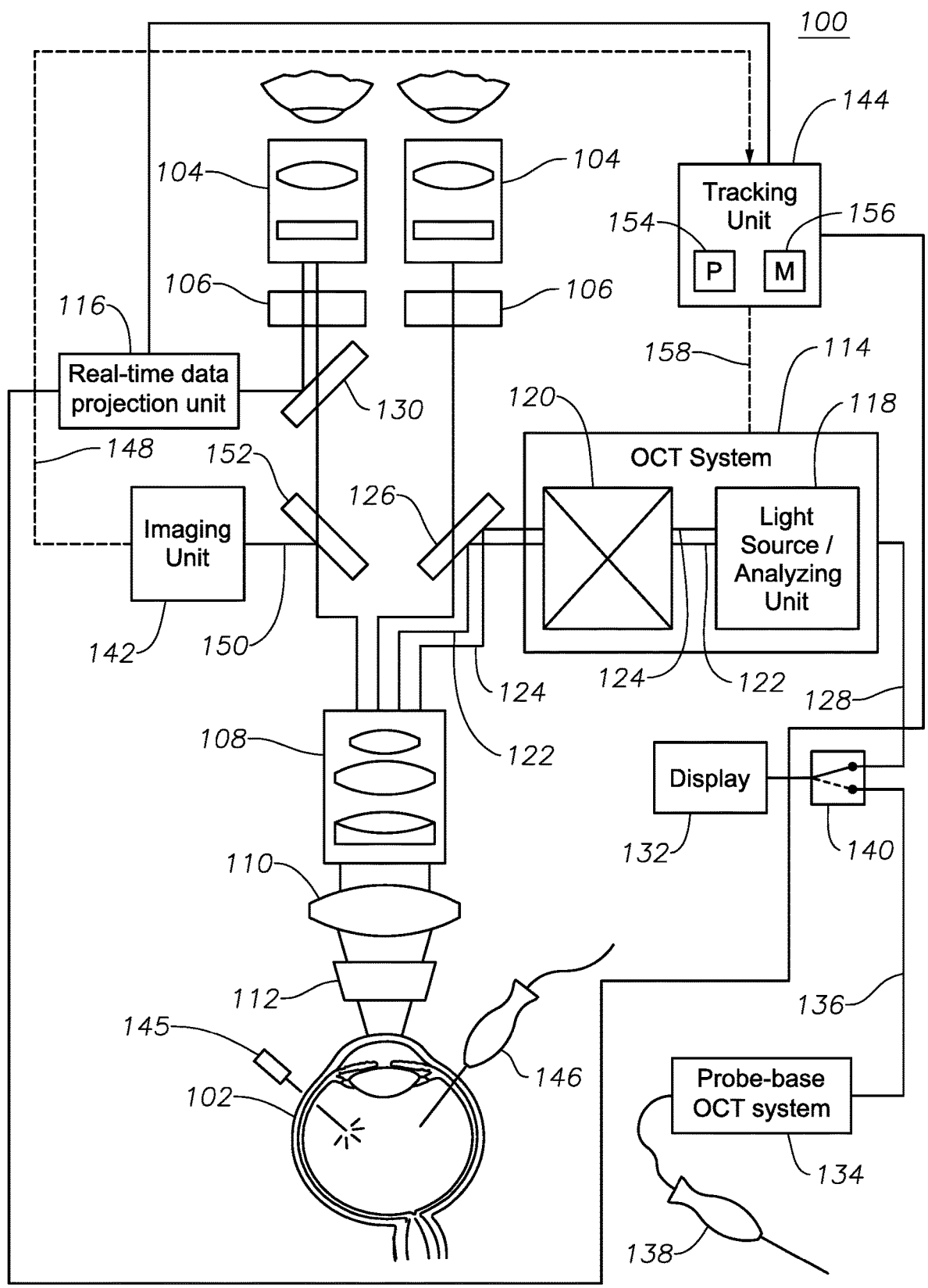
FIG. 1 illustrates an example of ophthalmic surgical visualization system that includes a surgical microscope and integrated OCT system, according to certain embodiments.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts. References to location, distance, or proximity herein may refer to actual and/or relative location(s), distance(s), or proximity(ies).

In general, the present disclosure relates to an ophthalmic surgical visualization system capable of providing one or more visual indicators that conveys the proximity of a surgical tool to particular tissue, such as the retina. Certain embodiments provide a user with a microscope image of eye tissue that includes a computer-generated visual indicator (e.g., a pointer, shape, icon, or other graphic element) which indicates an distance between particular eye tissue (e.g., a retina) and a surgical tool inserted in the eye (e.g., the tip of a vitrectomy probe). One or more characteristics of the visual indicator (e.g., its color, size, shape) may be modified in real-time to reflect the distance between the surgical tool and particular eye tissue. In certain embodiments, a characteristic of the visual indicator (e.g., size, color) is modified incrementally, and proportional to the change in distance, to intuitively convey the movement of the tool. The distance between the surgical tool and particular eye tissue may be determined based on data obtained by an imaging system capable of resolving depth in real time, such as an OCT imaging system, ultrasound imaging system, a multispectral imaging system, a computerized axial tomography (CAT) scan system, a magnetic resonance imaging (MRI) system, or a positron emission tomography (PET) imaging system. Certain embodiments also track movements of the surgical tool within a microscope image in real time, and may display the visual indicator as a dynamic overlay in the microscope image presented in an eyepiece or on a heads-up display. For example, a visual indicator may be displayed as a graphic overlay superimposed on a distal end of the surgical tool as it moves within in a microscope image of a retina, and the size and/or color of the overlay indicator may be updated continuously according to the distance between the distal end of the surgical tool and the retina.

FIG. 1 illustrates an example of an ophthalmic surgical visualization system according to particular embodiments of the present disclosure. Surgical microscope 100 includes integrated OCT and display systems. Surgical microscope 100 may facilitate magnified viewing of a patient's eye 102 during a surgical procedure and may generally include eyepieces 104, a relay lens 106, magnifying/focusing optics 108, an objective lens 110, and surgical viewing optics 112. Each of eyepieces 104, relay lens 106, magnifying/focusing optics 108, objective lens 110, and surgical viewing optics 112 may include any suitable optical components as understood by persons of ordinary skill in the art.

Surgical microscope 100 may additionally include an integrated OCT system 114 operable to generate OCT images of the patient's eye 102 and a real-time data projection unit 116 operable to display those OCT images to a surgeon via one or both eyepieces 104. The location at which OCT system 114 is integrated into surgical microscope 100 (as discussed in further detail below) may advantageously allow the OCT scan range to be automatically adjusted as a surgeon manipulates the microscope field of view via the magnifying/focusing optics 108. Moreover, real-time data projection unit 116 may advantageously allow a surgeon to view the OCT images generated by OCT system 114 without the need to look at a separate display monitor.

OCT system 114 may include a light source/analyzing unit 118 and a beam scanner 120. In general, light source/analyzing unit 118 may generate an OCT imaging beam 122 and beam scanner 120 (in conjunction with other optical components of the surgical microscope) may direct the generated OCT imaging beam 122 to a particular region within the patient's eye 102. Reflections of the OCT imaging beam 122 from the particular region within the patient's eye 102 (reflected OCT imaging beam 124) may return to light source/analyzing unit 118 along the same optical path as OCT imaging beam 122, and light source/analyzing unit 118 may generate OCT images of the particular region by determining interference between the reflections 124 and a reference arm of the OCT imaging beam 122. The present disclosure contemplates that OCT system 114 may include any suitable additional optical components for manipulating OCT imaging beam 122 as would be understood by those of skill in the art, and those additional components are not depicted/described for the sake of simplicity.

In certain embodiments, the OCT imaging beam 122 may comprise an infrared or near infrared light beam covering a relatively narrow band of wavelengths (e.g., 830 nm-870 nm, 790 nm-900 nm, 950 nm-1150 nm). However, an OCT imaging beam 122 having any suitable spectral range may be used.

In certain embodiments, the OCT imaging beam 122 may pass through beam scanner 120 (described in further detail below) along with any other suitable optical components of OCT system 114 (not depicted, as described above). OCT imaging beam 122 may then be directed to the patient's eye 104 via one or more of the above-described optical components of surgical microscope 100 (as described in further detail below).

Beam scanner 120 may comprise any suitable optical component or combination of optical components facilitating focusing of the OCT imaging beam 122 in the X-Y plane. For example, beam scanner 120 may include one or more of a pair of scanning mirrors, a micro-mirror device, a MEMS based device, a deformable platform, a galvanometer-based scanner, a polygon scanner, and/or a resonant PZT scanner. In certain embodiments, the position of the optical components of beam scanner 120 may be manipulated in an automated manner. As just one example, beam scanner 120 may comprise a pair of scanning mirrors each coupled to a motor drive, the motor drives operable to rotate the mirrors about perpendicular axes. As a result, by controlling the position of the coupled motors (e.g., according to a pre-determined or selected scan pattern), the X-Y positioning of OCT imaging beam 122 within the patient's eye 104 can be controlled. Additionally, the depth of focus of the OCT imaging beam 122 may be controlled by one or more other components of OCT system 114 as is understood in the art in order to facilitate 3-D OCT imaging.

As described above, reflected OCT beam 124 may return to OCT system 114 along substantially the same optical path as traveled by OCT imaging beam 122. Once reflected OCT beam 124 reaches light source/analyzing unit 118, light source/analyzing unit 118 may construct an OCT image (A-scan) based on interference between the reflected OCT beam 124 and a reference arm of OCT imaging beam 122 (as is known in the art). Moreover, by moving the imaging beam in the X-Y plane via beam scanner 120 and/or changing the depth of focus of the imaging beam 122, a plurality of OCT images (A-scans) may be generated and combined into an OCT cross sectional image (B-scan), and a plurality of those cross sectional images (B-scans) may be combined to generate a 3-D OCT image.

In certain embodiments, OCT system 114 may be integrated into surgical microscope 100 via a beam coupler 126 located in the optical path of the surgical microscope 100. Beam coupler 126 may include an optical element configured to reflect wavelengths in the spectral range of the OCT imaging beam 122 (e.g., infrared wavelengths) while allowing passage of light in the visible spectrum passing through surgical microscope 100. As one example, beam coupler 126 may comprise one of a dichroic hot mirror, a polarizing beamsplitter, and a notch filter.

In certain embodiments, OCT system 114 may be integrated into surgical microscope 100 via a beam coupler 126 located in the optical path of the surgical microscope 100. Beam coupler 126 may include an optical element configured to reflect wavelengths in the spectral range of the OCT imaging beam 122 (e.g., infrared wavelengths) while allowing passage of light in the visible spectrum passing through surgical microscope 100. As one example, beam coupler 126 may comprise one of a dichroic hot mirror, a polarizing beamsplitter, and a notch filter.

In certain embodiments, beam coupler 126 may be located along the optical path between the surgical viewing optics 112 and an eyepiece 104. Surgical viewing optics 112 may include a drop-on macular lens, contact-based wide-angle lens, noncontact-based viewing system such as (binocular indirect ophthalmomicroscope) BIOM, or any other suitable viewing optics. More particularly, beam coupler 126 may be located along the optical path between magnifying/focusing optics 108 and an eyepiece 104. As a result, OCT imaging beam 122 will pass through magnifying/focusing optics 108, allowing the OCT scan range to be automatically adjusted as a surgeon manipulates the microscope field of view via the magnifying/focusing optics 108. The present disclosure contemplates that, although not depicted, OCT system 114 may additionally include any suitable optical components facilitating appropriate focus of OCT imaging beam 122 within the patient's eye 102 in light of the fact that the OCT imaging beam 116 passes through magnifying/focusing optics 108 and objective lens 110.

In certain embodiments, OCT system 114 may generate a visible aiming beam (not depicted) in addition to OCT imaging beam 122. This visible aiming beam may be visible to the surgeon via eyepieces 104 and may assist the surgeon in directing OCT imaging. In such embodiments, beam coupler 126 may be configured to reflect both the spectral range of the OCT imaging beam 122 (e.g., infrared wavelengths) and a narrow band of visible light (the aiming beam falling within that narrow band) while allowing passage of visible light passing through surgical microscope 100 that falls outside the narrow band of the aiming beam.

The OCT image(s) generated by OCT system 114 (identified in FIG. 1 by reference numeral 128), which may include an A-scan, a B-scan, or a 3-D OCT image constructed by combining a plurality of B-scans as described above, may be communicated to real-time data projection unit 116 for display to a surgeon via one or both eyepieces 104.

The present disclosure contemplates that, although not depicted, certain embodiments may include one or more additional or alternative depth-imaging systems, such as an ultrasound imaging system, a multispectral imaging system, a computerized axial tomography (CAT) scan system, a magnetic resonance imaging (MRI) system, or a positron emission tomography (PET) imaging system. Such imaging systems may be configured analogously to the OCT imaging systems described herein (e.g., integrated with microscope 100, probe-based, and/or integrated with surgical instrument 146) to generate depth-resolved images that may be analyzed by tracking unit 144.

Real-time data projection unit 116 may include any suitable device for projecting an image and may include any suitable optics (not depicted) for focusing that image. For example, real-time data projection unit 116 may comprise one of a heads-up-display, a one-dimensional display array, a two-dimensional display array, a screen, a projector device, or a holographic display.

Real-time data projection unit 116 may be integrated into surgical microscope 100 via a beam splitter 130 located in the optical path of the surgical microscope 100. Beam splitter 130 may include an optical element configured to reflect the projected image generated by real-time data projection unit 116 toward eyepiece(s) 104 without substantially interfering with visible light reflected from the patient's eye 102.

In certain embodiments, surgical microscope 100 may additionally or alternatively include a probe-based OCT system 134. Probe-based OCT system 134 may generate OCT images 136 is substantially the same manner as described above with regard to OCT system 114 except that the OCT imaging beam generated by probe-based OCT system 134 may be directed within the patient's eye 102 using a probe 138 that may be inserted into the patient's eye 102. In embodiments including both an OCT system 114 and a probe-based OCT system 134, surgical microscope 100 may additionally include a source selection unit 140. Source selection unit 140 may include any suitable switch allowing selection either OCT images 128 (generated by OCT system 114) or OCT images 136 (generated by probe-based OCT system 134) for communication to real-time data projection unit 116 or display 132. As a result, a surgeon may select which OCT imaging system to use for imaging during surgery.

In certain embodiments, surgical instrument 146 may additionally or alternatively be integrated with OCT imaging probe 138 or include an additional or alternative OCT imaging probe. For example, surgical instrument 146 may be communicatively coupled with probe-based OCT system 134. Surgical instrument 146 may include one or more optical fibers and extending down the length of the instrument toward its distal tip to transmit and/or receive an OCT imaging beam or reflected light from eye 102. The fibers may terminate at or near the distal tip to transmit an imaging beam into eye 102. Such fibers and other components of surgical instrument 146 may be configured to transmit an OCT imaging beam to eye 102 and return reflections to light source/analyzing unit 118. In this manner, the OCT imaging beam may be directed within the patient's eye 102 using surgical instrument 146 rather than a separate OCT probe or beam scanner. In such embodiments, the distance between the distal tip of surgical instrument 146 and eye 102 may be determined without adjusting an OCT beam toward the instrument; because the imaging beam is projected from the tip of the surgical instrument, it is not necessary to adjust an external OCT imaging beam to encompass both the eye tissue and the surgical instrument within imaging field. In certain embodiments, surgical instrument 146 may be integrated with or include a depth imaging probe other than an OCT imaging probe.

OCT images projected by real-time data projection unit 116 (e.g., OCT images 128 and/or OCT images 136) may be displayed as a semitransparent overlay aligned with the visible structures viewed by the surgeon via eyepieces 104. In such embodiments, alignment between the OCT images and the actual structures of the eye may be achieved, for example, based on retinal tracking (described further below), instrument tracking (described further below), an aiming beam, or any combination thereof.

In certain other embodiments, the OCT images projected by real-time data projection unit 116 may be displayed in a corner of the field of view of the surgeon or any other suitable location in which they do not substantially impair the surgeon's ability to view the eye 102 through eyepieces 104.

Although real-time data projection unit 116 is described above as projecting OCT images 128 and/or OCT images 136 into the optical path of the surgical microscope 100 such that they are viewable through eyepiece(s) 104, the present disclosure contemplates that real-time data projection unit 116 may, additionally or alternatively, project any other suitable information (e.g., extracted and/or highlighted information from OCT data, fundus images, surgical parameters, surgical patterns, surgical indicators, etc.) into the optical path of the surgical microscope 100, according to particular needs.

Surgical microscope 100 may additionally include an imaging unit 142 and a tracking unit 144. Tracking unit 144 may be communicatively coupled (via wired or wireless communication) to OCT system 114, real-time data projection unit 116, and display 132 to provide images, indicators, and other data for display to a system operator. As described in further detail below, OCT system 114, imaging unit 142, and tracking unit 144 may collectively facilitate tracking the location, depth, proximity, and movement of a surgical instrument 146 within the patient's eye 102.

Imaging unit 142 may include any suitable device for generating a fundus image 148 of a patient's eye 102 and may include suitable magnification and focusing optics (not depicted) for performing that function. As a simplified example, visible or near infrared light 150 reflected by the patient's eye 102 along the optical path of surgical microscope 100 may be directed toward imaging unit 142 via a mirror 152 placed along the optical path and operable to partially reflect such light. In certain embodiment, fundus images 148 may be discrete still photographs of the patient's eye 102. In other embodiment, the fundus image 148 may comprise a continuous video stream of the patient's eye 102. Fundus image 148 may comprise multiple image frames that can be processed and modified by other components of system 100. Example imaging units may include digital video cameras, line scan ophthalmoscopes or confocal-scanning ophthalmoscopes.

In the depicted embodiment, because the visible or near infrared light 150 is sampled from the optical path before OCT images are introduced into the optical path via real-time data projection unit 116, the generated fundus images 148 will not include the projected OCT images (which may be beneficial for the instrument tracking described below). Although imaging unit 142 is depicted and described as being located at particular position relative to the optical components of the surgical microscope 100 and OCT system 114, the present disclosure contemplates that imaging unit 142 may be placed at any suitable location relative to those components, according to particular needs.

Tracking unit 144 of surgical microscope 100 is operable to determine location/position, depth, proximity, and motion of surgical instrument 146 within the patient's eye 102 based at least in part on fundus images 148 generated by imaging unit 142 and depth-resolved or three-dimensional images generated by a depth imaging system, such as OCT system 114, an ultrasound imaging system, a multispectral imaging system, a computerized axial tomography (CAT) scan system, a magnetic resonance imaging (MRI) system, or a positron emission tomography (PET) imaging system.

Tracking unit 144 may include any suitable combination of hardware, firmware, and software. In certain embodiments, tracking unit 144 may include processor 154 and memory 156. Processor 154 may include one or more microprocessors, field-programmable gate arrays (FPGAs), controllers, or any other suitable computing devices or resources. Processor 154 may work, either alone or with other components depicted in FIG. 1, to provide the functionality described herein. Memory 156 may take the form of volatile or non-volatile memory including, without limitation, magnetic media, optical media, random access memory (RAM), read-only memory (ROM), removable media, or any other suitable memory component. Memory 156 may store instructions for programs and algorithms that, when executed by processor 154, implement the functionality of tracking unit 144.

Tracking unit 144 may be programmed to (or may store software in memory 156 that, when executed by processor 154, is operable to) analyze fundus images 148 to determine and track the location of surgical instrument 146. For example, processor 154 may receive and process or analyze images 148 acquired by imaging unit 142, and may generate indicators and images for display by real-time data projection unit 116 or display 132 based on the processed images. Processor 154 may process or analyze multiple images to track changes in the location of surgical instrument 146, and modify the indicators and images to reflect such changes. Memory 156 of tracking unit 144 may store the pre-processed and/or post-processed image data. Processor 154 may detect and calculate the location and/or orientation (or the change of the location and orientation) of surgical instrument 146 in the surgical field based on the fundus images 148.

Additionally, tracking unit 144 may be programmed to (or may store software in memory 156 that, when executed by processor 154, is operable to) determine the depth of distal tip 149 and its proximity to particular tissue of eye 102. For example, processor 154 may receive three-dimensional or depth-resolved imaging data acquired by OCT system 114 (or an alternative depth imaging system) and may analyze the data to determine a distance between and/or proximity of distal tip 149 and the retina of eye 102. Based on the determined distance, tracking unit 144 may generate an indicator for display by real-time data projection unit 116 or display 132 to alert a system operator about the proximity of distal tip 149 to particular eye tissue, such as the retina. Processor 154 may continuously or repeatedly determine or calculate location, orientation, and distance/proximity data related to distal tip 149 to track distal tip 149 and update the indicator to provide a real-time indication of the position of distal tip 144 in the microscope image and the distance between distal tip 144 and the retina of eye 146. Processor 154 may also continuously or repeatedly modify a characteristic of the visual indicator (e.g., size, color) incrementally and proportionally to the change in distance between distal tip 149 and the retina of eye 102 to intuitively convey the movement of distal tip 149. Memory 156 of tracking unit 144 may store the pre-processed and/or post-processed depth imaging data.

Further, tracking unit 144 may be programmed to (or may store software in memory 156 that, when executed by processor 154, is operable to) generate signals 158 to be communicated to OCT system 114 to cause beam scanner 120 of OCT system 114 to direct the location of the OCT imaging beam 122 within the patient's eye 102. For example, signals 158 may be generated based on the determined location of the surgical instrument 146 within the patient's eye 102, and beam scanner 120 of OCT system 114 may direct OCT imaging beam 122 to a location in the vicinity of the distal tip 149 of surgical instrument 146. As a result, the OCT images 128 may be generated in an area of most interest to the surgeon, and tracking unit 144 may calculate the distance between distal tip 149 and the retina throughout a procedure using data generated by OCT system 114. Moreover, in embodiments in which the OCT images 128 are displayed as a semi-transparent overlay in the field of view of the microscope, the tracking of the surgical instrument 146 may additionally facilitate proper positioning of that overlay.

As another example, the signals 158 may be generated based on a determined location of the retina of the patient's eye 102 (determined by tracking unit 144 by processing fundus images 148 in a manner similar to that discussed herein with regard to tracking surgical instrument 146), and beam scanner 120 of OCT system 114 may direct OCT imaging beam 122 to constant location relative to the retina. Moreover, in embodiments in which the OCT images 128 are displayed as a semi-transparent overlay in the field of view of the microscope, the tracking of the retina may additionally facilitate proper positioning of that overlay.

Although surgical microscope 100 is depicted and described as including OCT images displayed through a fixed, single channel (i.e., real-time data projection unit 116 is coupled to the optical path of one of the two eyepieces 104), other embodiments are contemplated by the present disclosure (as described with regard to FIGS. 7-10, below).

The functionality and operation of tracking unit 144 will now be discussed in additional detail, in accordance with certain embodiments.

Tracking unit 144 may use various techniques to determine and track the location of surgical instrument 146 within a microscope image (e.g., the X-Y position of distal tip 149 within a microscope image). In certain embodiments, surgical instrument 146 may have attached or embedded sensing devices. For example, surgical instrument 146 may have one or more gyroscopes, accelerometers, gravity sensors, linear acceleration sensors, rotation vector sensors, geomagnetic field sensors, or other types of sensors, to sense changes in position, location, or movement. Data generated from such sensors may be provided to tracking unit 144, which may analyze the data to determine the location, position, and/or movement of surgical instrument 146.

In certain embodiments, tracking unit 144 may use image-based processing techniques to determine and track the location of surgical instrument 146. For example, tracking unit 144 may employ machine vision or computer vision algorithms to images acquired from imaging unit 142 to determine and track the location of surgical instrument 146. Tracking unit 144 may apply feature recognition or extraction techniques and/or motion-based object tracking and image processing algorithms (e.g., edge detection, corner detection, blob detection, blob extraction, ridge detection, scale-invariant feature transform, motion detection, background subtraction, frame difference, optical flow, thresholding, template matching, Hough transform, etc.). Additionally or alternatively, tracking unit 144 may use region-based object tracking techniques.

For example, tracking unit 144 may apply feature recognition or extraction techniques (e.g., edge detection, corner detection, blob detection, blob extraction, ridge detection, scale-invariant feature transform, motion detection, optical flow, thresholding, template matching, Hough transform, etc.) to depth-resolved images to detect or isolate distal tip 149 and the retina of eye 102 within image data obtained by a depth imaging system. Tracking unit 144 may obtain and store a reference image of eye 102, and may compare images obtained during a surgical procedure with the reference image to determine the location and movement of, and distance between, a distal tip of surgical instrument 146 and the retina in eye 102.

Figure 2:
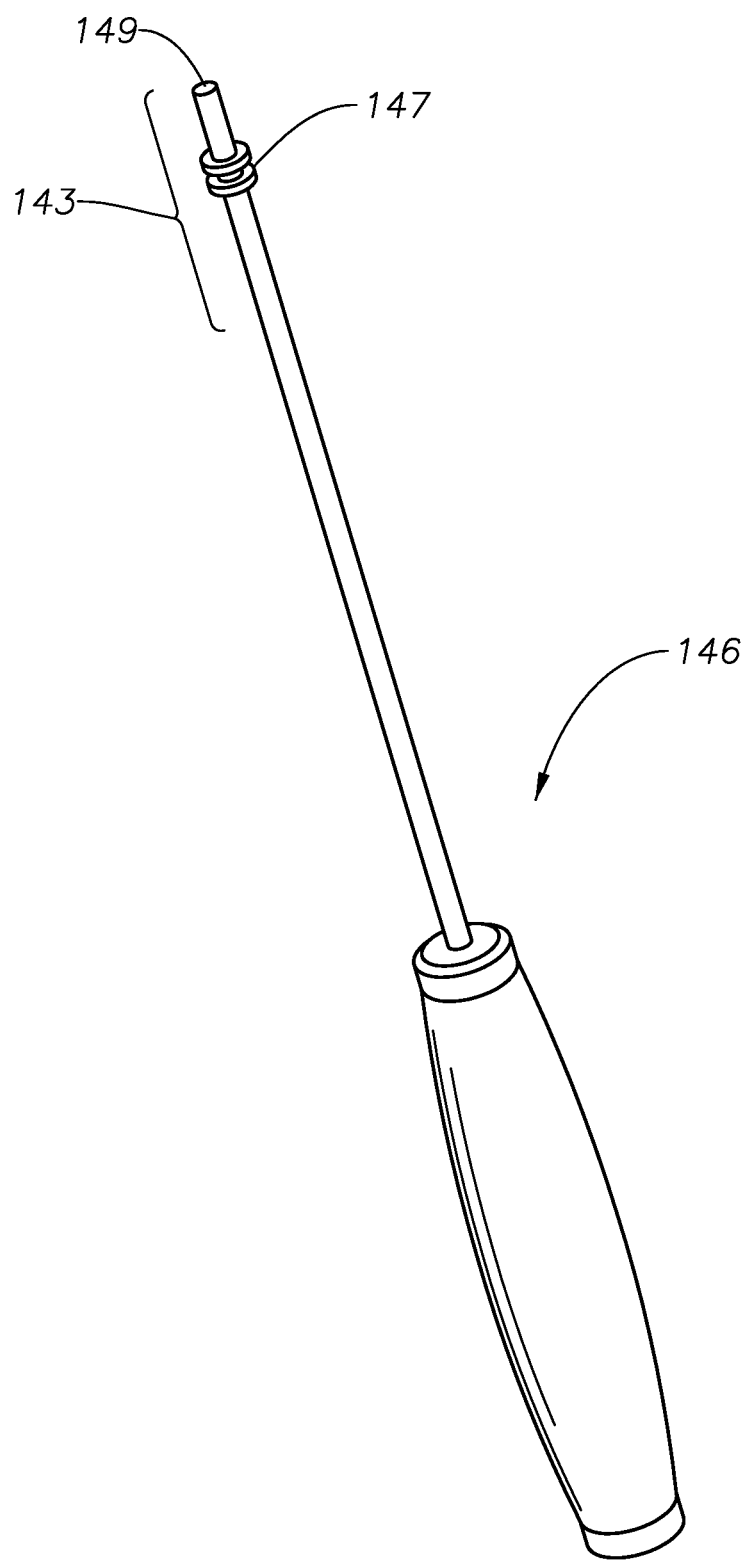
FIG. 2 illustrates an exemplary surgical instrument for use with a visualization system, according to certain embodiments.
Figure 3A:
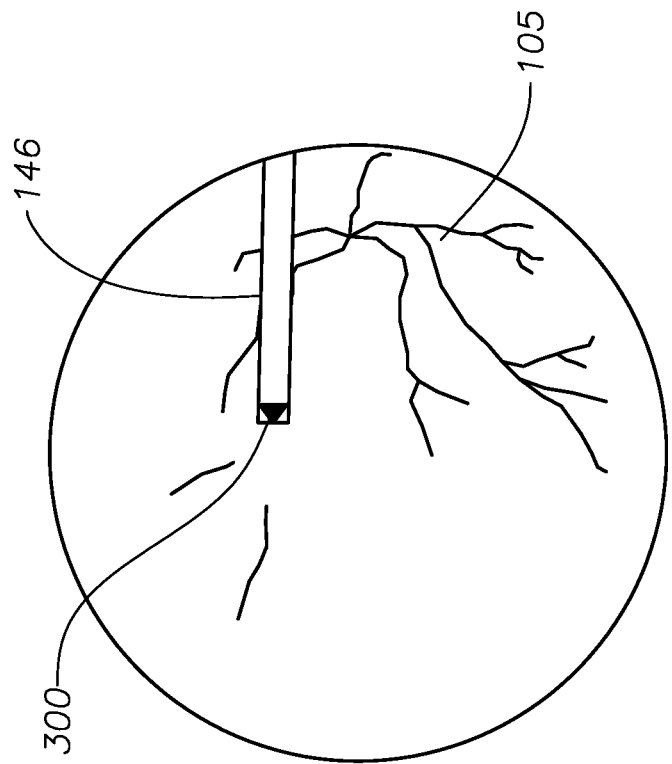
FIGS. 3A-3C illustrate microscope images including a visual indicator provided by a visualization system, according to certain embodiments.
Figure 3A:
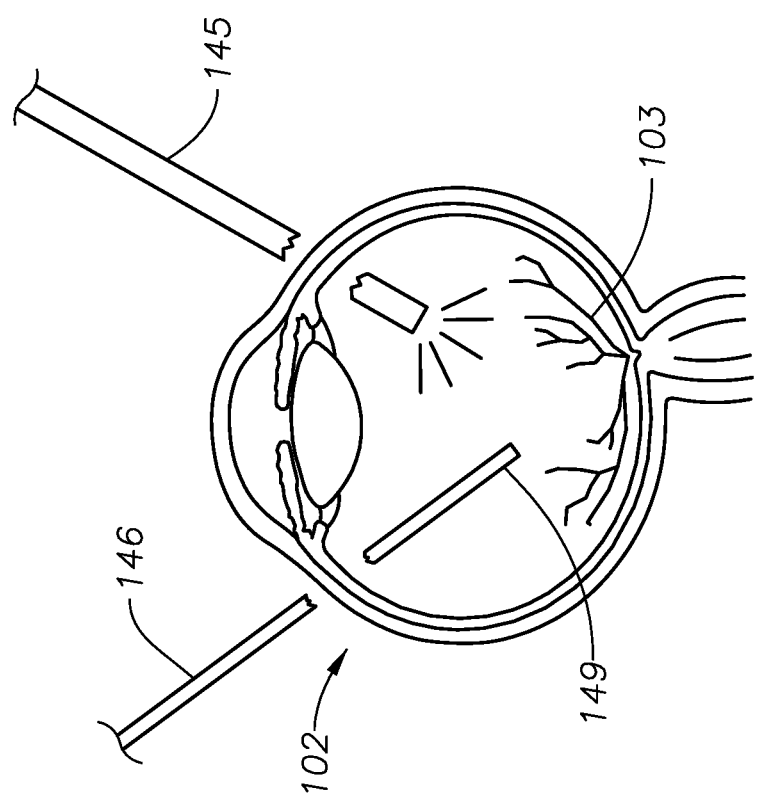
Figure 3B:
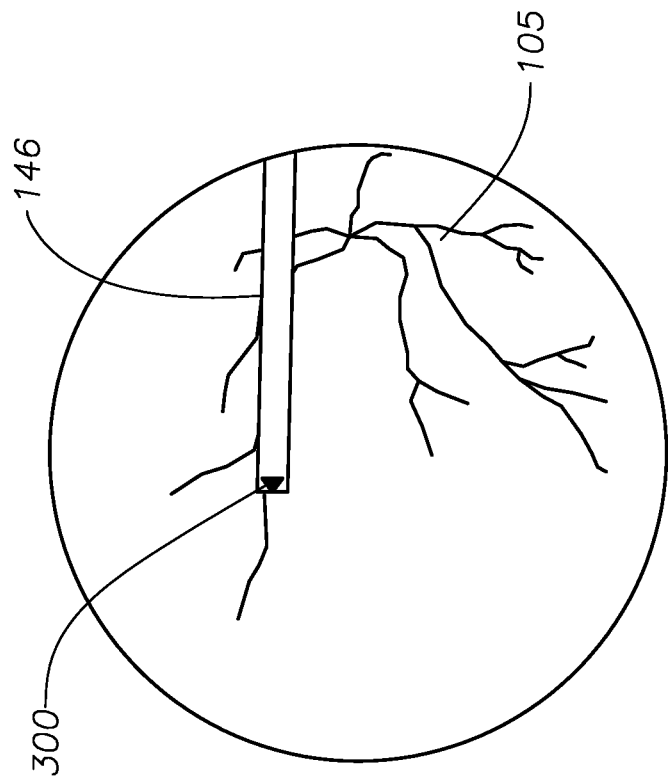
Figure 3B:
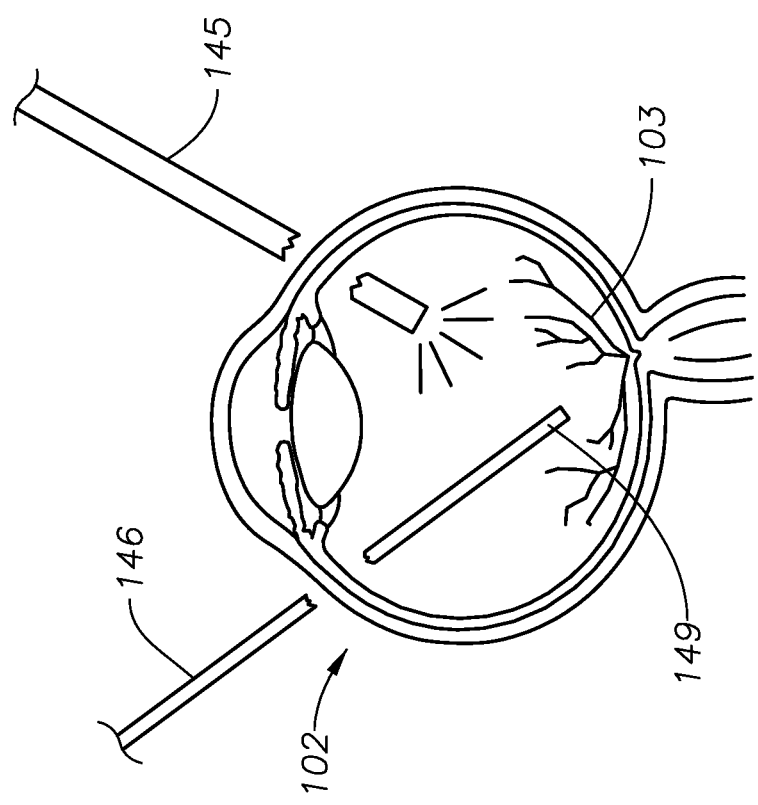
Figure 3C:
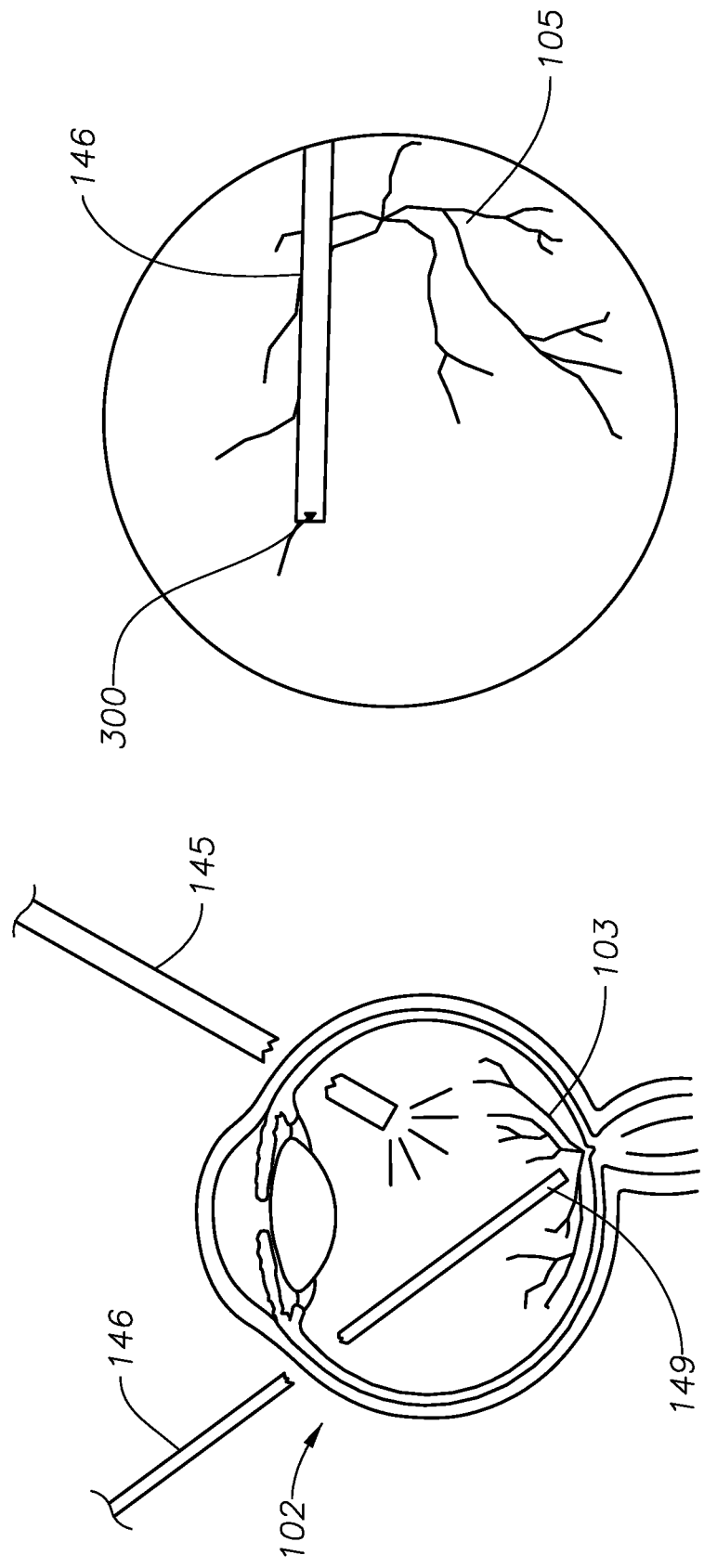
Figure 4A:
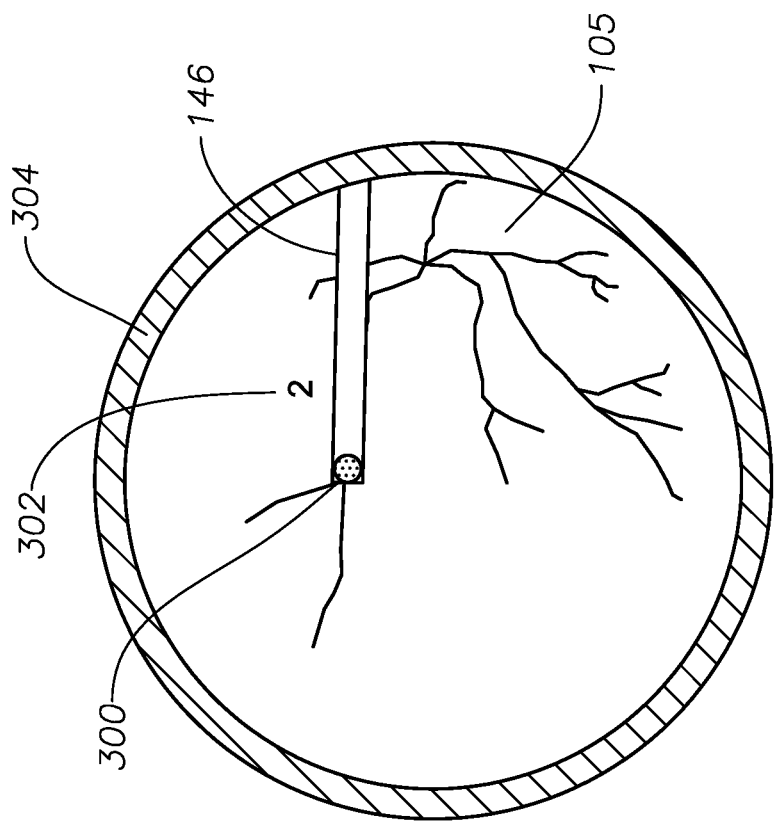
FIGS. 4A-4C illustrate microscope images including various alternative visual indicators provided by a visualization system, according to certain embodiments.
Figure 4A:
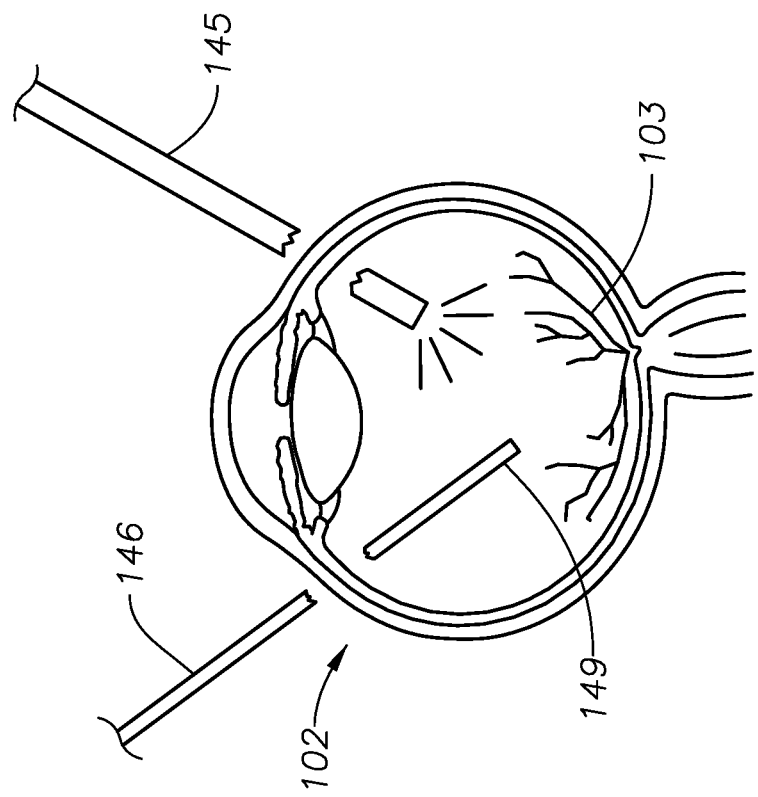
Figure 4B:
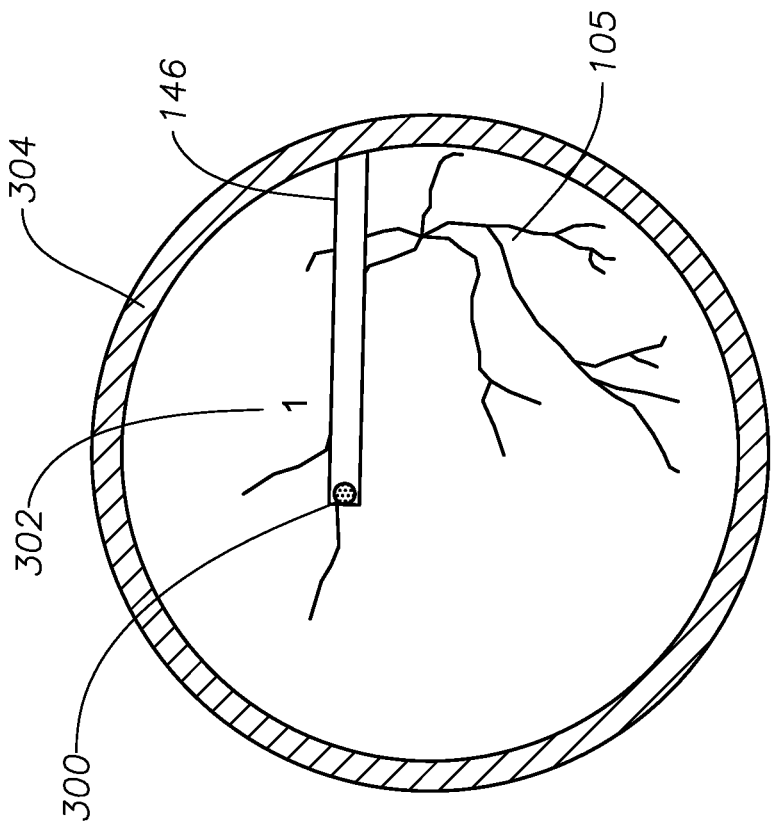
Figure 4B:
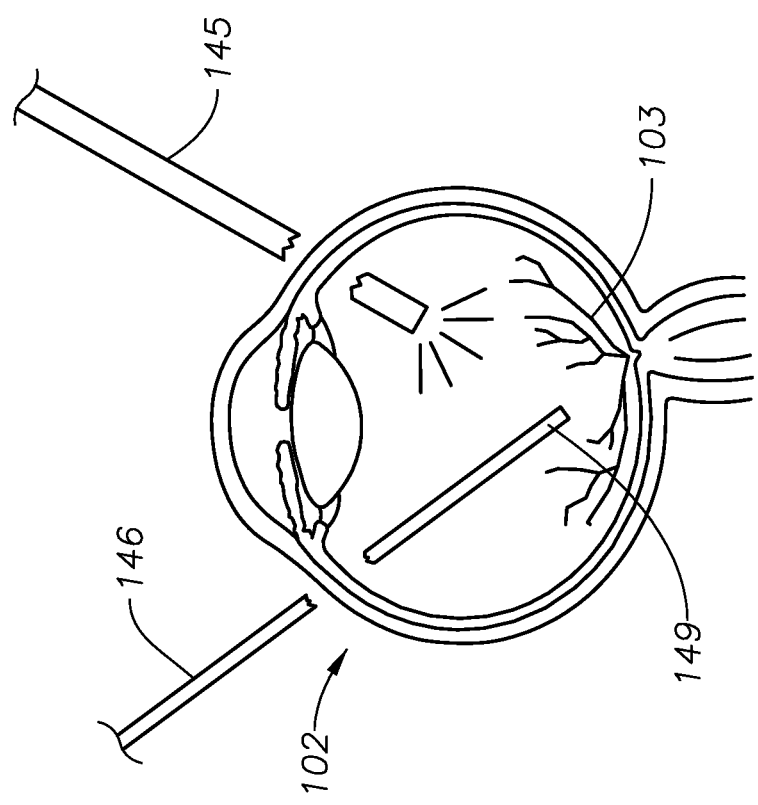
Figure 4C:
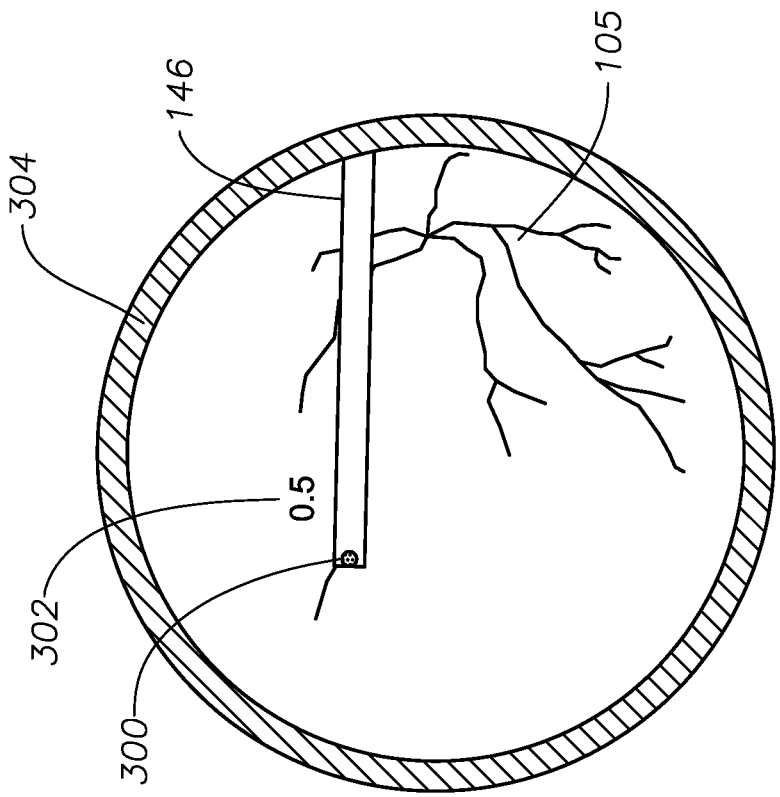
Figure 4C:
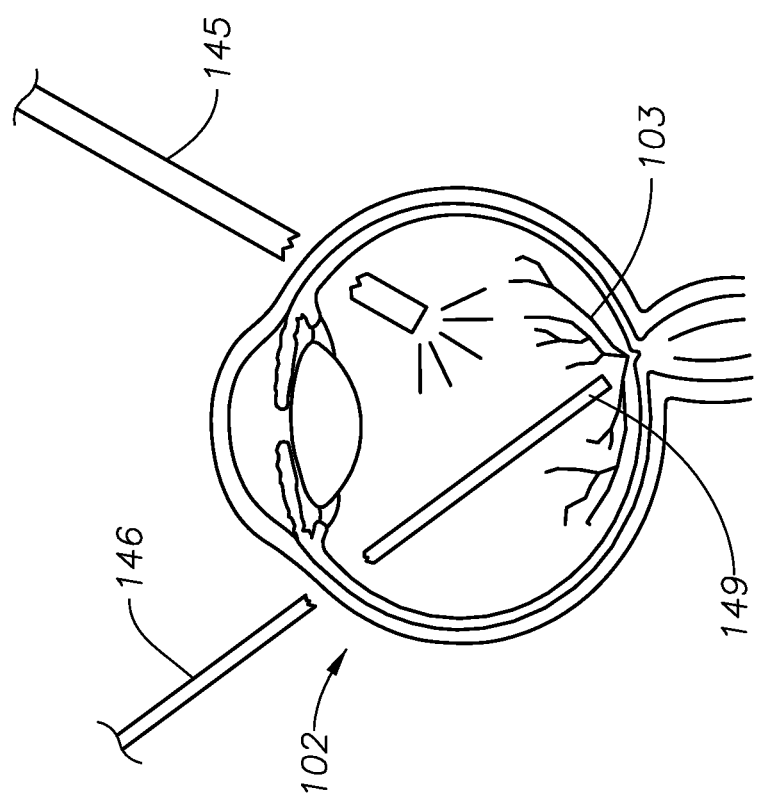

According to certain embodiments, tracking unit 144 may be programmed to determine and track the location of surgical instrument 146 using feature-based object tracking to extract and search for unique features of surgical instrument 146 (e.g., a contour, edge, shape, color, corner/interest point, etc.) within an image received from imaging unit 142. In such embodiments, tracking unit 144 may use marker 147 to assist in determining and tracking the location of surgical instrument 146. As shown in FIG. 2, surgical instrument 146 may include a marker 147 positioned at or near a distal portion 144 which has a high contrast feature in the visible light or infrared spectrum, or other spectral ranges detectable by imaging unit 142. High contrast may be obtained by using a color or pattern distinguishable from colors or patterns in the fundus of eye 102. A light source 145 such as endo-illuminator or a fiber illuminator may emit an imaging light to illuminate a fundus of eye 102. Marker 147 is discussed in additional detail below with respect to FIG. 6.

Tracking unit 144 may also determine and track the distance and proximity between surgical instrument 146 and tissues in eye 102. In certain embodiments, tracking unit 144 receives depth-resolved image data from OCT imaging system 114 or an alternative depth imaging system capable of determining tissue and instrument depth and position. Tracking unit 144 may apply image-based processing techniques to such image data in order to determine and/or extract location and position data related to surgical instrument 146 and tissues in eye 102. Based on this analysis, tracking unit 144 may calculate a distance between parts of surgical instrument 146 (e.g., distal tip 149) and tissue in eye 102 (e.g., the retina). Tracking unit 144 may track changes in this distance by processing a stream of image data obtained by the depth imaging system in real time. Tracking unit 144 may also store image analysis data in order to calculate and track changes in the location and movement of, and distance between, surgical instrument 146 and tissues in eye 102.

In certain embodiments, tracking unit 144 receives image data from a depth resolved imaging system, such as OCT system 114. Tracking unit 144 may be configured to analyze depth-resolved images to identify features depicted in the image, such as a retina and/or surgical tools. Tracking unit 144 may register depth image data and identify the coordinates of identified features in the depth-resolved image. Such coordinates may be digitized using computer vision or machine vision algorithms, such as edge or blob detection, and may be used to calculate the distance between features within the image.

In certain embodiments, a calibration sample material may be used to form a 3-D array of reference marks at location within known position coordinates. A depth-resolved image (e.g., an OCT image) may be obtained to establish a mapping relationship between known position coordinates of the reference marks and the depth-resolved images of the reference marks in the obtained depth-resolved image. This mapping relationship may be stored as digital calibration data and may be used to calculate the distance between features in the depth-resolved image (e.g., a retina and a cutting tip of a surgical tool) and for controlling the imaging beam of the depth-resolved imaging system.

In embodiments in which the depth-resolved imaging probe is separate from surgical instrument 146, the depth-resolved image may depict features that include a surgical instrument 146 and the retina of eye 102. For example, tracking unit 144 may receive depth-resolve images (e.g., A-scans or B-scans) that depict the retina of eye 102 and the distal tip surgical instrument 146. Tracking unit 144 may determine the distance or proximity between the retina of eye 102 and the distal tip of surgical instrument 146 based on characteristics of the received depth image. For example, in such images, the retina of eye 102 and the distal tip of surgical instrument 146 may appear separated by a space within the image (provided they are not in contact). Tracking unit 144 may determine the distance or proximity between the retina of eye 102 and the distal tip of surgical instrument 146 based on the degree of separation between them in the image. For example, digitized coordinates may be used as discussed above. As another example, tracking unit 144 may determine the distance or proximity based on the number of pixels separating retina of eye 102 and the distal tip surgical instrument 146 in a depth-resolved image, which may have a fixed z-depth resolution. In a depth-resolved image having a fixed z-depth (such as OCT images), distance and/or proximity between features in the image (e.g., a tool top and the retina) may be calculated based on pixels, which individually correspond to a fixed distance. Tracking unit 144 may identify and process pixel counts in the depth-resolved image to determine the distance between imaged objects. To facilitate this approach, tracking unit 144 may advantageously cause the depth imaging system to direct the depth imaging beam to a location in the vicinity of surgical instrument 146, as described above.

In certain embodiments, tracking unit 144 may receive image data from a depth resolved imaging probe that is at least partially integrated within surgical instrument 146. In one example, surgical instrument 146 may include an integrated depth-imaging probe. Surgical instrument 146 may include one or more optical fibers used by a depth-imaging system (e.g., OCT system 114) to transmit an imaging beam, transmit reflected light from the eye, and generate a depth-resolved image (e.g., A-scans or B-scans) of eye 102. Such depth-resolved images may depict the retina of eye 102, without depicting surgical instrument 146 (because such images are obtained from the vantage point of the tip of instrument 146). Tracking unit 144 may determine the distance or proximity between the retina of eye 102 and the distal tip of surgical instrument 146 based on characteristics of the received depth image. For example, as discussed above, digitized coordinates may be used, or tracking unit 144 may identify and process pixel counts in the depth-resolved image to determine the distance between imaged objects. In certain embodiments, tracking unit 144 may determine the distance or proximity based on the pixels between the edge of the image (or other feature corresponding to the distal tip of surgical instrument 146) and a retina of eye 102 depicted in a depth-resolved image, which may have a fixed z-depth resolution. As noted above, in a depth-resolved image having a fixed z-depth (such as OCT images), distance and/or proximity between features in the image (e.g., a tool and a retina) may be calculated based on pixels, which correspond to a fixed distance. In such embodiments, the proximity of the surgical tool to eye tissue can be continuously determined without actively directing an imaging beam toward the surgical instrument 146.

Tracking unit 144 may additionally or alternatively use various image-based processing techniques (e.g., machine vision or computer vision algorithms, motion-based object tracking algorithms, region-based object tracking techniques, and/or feature-based object tracking) to analyze depth-resolved images (e.g., OCT images) and determine and track the distance between surgical instrument 146 and tissues in eye 102. For example, tracking unit 144 may apply feature recognition or extraction techniques (e.g., edge detection, corner detection, blob detection, blob extraction, ridge detection, scale-invariant feature transform, motion detection, optical flow, thresholding, template matching, Hough transform, etc.) to depth-resolved images to detect or isolate distal tip 149 and the retina of eye 102 within image data obtained by a depth imaging system. Tracking unit 144 may obtain and store a reference image of eye 102, and may compare images obtained during a surgical procedure with the reference image to determine the location and movement of, and distance between, a distal tip of surgical instrument 146 and the retina in eye 102.

Tracking unit 144 may generate an indicator (e.g., a number, shape, color, figure, or symbol, or other graphic element) for display by real-time data projection unit 116 or display 132 to identify the location, orientation, and depth of distal tip 149, and its proximity to the retina. For example, tracking unit 144 may generate an indicator (e.g., a dot or arrow) and overlay the indicator into a microscope image at the position of distal tip 149, thereby highlighting its location without interfering with a surgeon's view of surrounding tissue. In certain embodiments, tracking unit 144 applies the indicator as an overlay at the determined location of distal tip 149 in image 148. In other embodiments, the indicator may be an overlay located elsewhere in the microscope image. Processor 154 may track the location, orientation, and depth/proximity of distal tip 149 in order to provide a dynamic indicated updated in real time. Accordingly, the indicator may assist a surgeon by providing an accurate, real-time indication of the distance between distal tip 149 and the retina, which may be difficult to precisely discern from a stereo microscope image.

Tracking unit 144 may generate and communicate a signal specifying the position of the indicator in an image to cause real-time data projection unit 116 or display 132 to project or display the indicator as an overlay on a microscope image. Tracking unit 144 may alternatively generate a modified fundus image that includes the indicator overlay, and communicate the modified image to real-time data projection unit 116 or display 132 for presentation to a user.

In some examples, an aspect of the indicator may directly indicate the distance between distal tip 149 and the retina. For example, the indicator may be a numerical value specifying the distance (e.g., "2.0" for 2.0 mm, "1.0" for 1.0 mm, and "0.5" for 0.5 mm)). In some examples, tracking unit 144 may generate an indicator having a particular characteristic (e.g., size, shape, color, flash rate, brightness, transparency, quantity, etc.) that indirectly indicates the distance between distal tip 149 and the retina of eye 102. Additionally, the indicator may be modified or adjusted as the distance between distal tip 149 and the retina of eye 102 changes. In certain embodiments, a characteristic of the visual indicator (e.g., size, color) is modified incrementally, and proportional to the change in distance, to intuitively convey the movement of distal tip 149.

In certain embodiments, tracking unit 144 may associate particular colors with particular distances between distal tip 149 and the retina. For example, tracking unit 144 may associate a green indicator with a distance of 2 mm or more, a yellow indicator with a distance of 1 mm, and red indicator with distances of less than 0.5 mm. The color scheme may be gradated so that the indicator transitions from green to yellow to red in intermediate shades as the distance decreases from 2 mm to 0.5 mm. The incremental change in color may be proportional to the incremental change in distance.

In certain embodiments, tracking unit 144 may associate a particular indicator size with particular distances, such that the generated indicator will become gradually larger or smaller as the distance between distal tip 149 and the retina of eye 102 decreases. For example, tracking unit 144 may generate a visual indicator as a triangular overlay on distal tip 149 that becomes larger as it moves away from the retina and smaller as it approaches the retina. Tracking unit 144 may associate smaller sizes with greater depths of distal tip 149, to provide the impression that the indicator is moving away from the system operator as it approaches the retina. The incremental change in size may be proportional to the incremental change in distance. Tracking unit 144 may also set upper and lower limits on the size of the indicator so as to avoid obstructing the surgeon's view of surrounding tissue or scenarios where the indicator may become too small to be seen clearly.

Any number of indicator characteristics may be modified to indicate distance. In some examples, as the distance between distal tip 149 and the retina of eye 102 decreases, tracking unit 144 modifies the indicator to become increasingly brighter, transition from transparent to opaque, begin flashing, flash at an increasing rate, and/or change shape or form. For example, tracking unit 144 may cause an indicator to flash when the distance between distal tip 149 and retina is less than a preset threshold, such as 0.5 mm.

Some examples may utilize a combination of indicator characteristics to indicate distance. For example, tracking unit 144 may associate a minimum indicator size with a distance threshold (to avoid decreasing the size of the indicator further), and may modify the indicator to become a different color, grow brighter, and/or flash as the distance exceeds the threshold.

Incrementally-adjustable or continuously variable characteristics such as size, color, flash rate, brightness, etc. advantageously allow the characteristic to be modified in proportion to the incremental change in distance. Correlating indicator changes to distance in this manner advantageously provides a surgeon with an intuitive indication of distance, and changes in distance, that can be easily monitored during a procedure.

Certain embodiments may modify the position or location of an indicator based on distance. For example, certain embodiments may provide a visual indicator that appears only when a distance between distal tip 149 and the retina drops below a threshold (e.g., 2 mm). As another example, certain embodiments may display a visual indicator in a first location when tissue of eye 102 and surgical instrument 146 are separated by at least a threshold distance (e.g., near the outer edge of the microscope image), and relocate the visual indicator to a second location (e.g., near distal tip 149) when the threshold is met.

In certain embodiments, the indicator may additionally or alternatively indicate an orientation, e.g., a pointing angle, of surgical instrument 146. For example, an arrow may be used as the indicator to indicate the pointing direction of surgical instrument 146. The indicator may also include an image, such as an OCT image of a region of a retina of eye 102, or a surgical setting parameter, such as a cutting speed of a vitrectomy probe.

Various embodiments of tracking unit 144 may allow a user to configure the appearance, characteristics, and behavior of the indicator. For example, a user may configure a particular size and shape for an indicator, and may configure how the indicator is modified to indicate distance. Certain embodiments of tracking unit 144 include a user interface to receive user input regarding customized settings defining when, where, and how the visual indicator will be displayed and modified. In certain embodiments, a user may control whether a visual indicator is displayed via a pedal, switch, soft key, console button, voice command, or other input mechanism. The visual indicator may also be configured to appear based on a timer, particular movements of surgical instrument 146, or the position or location of surgical instrument 146 and/or distal tip 149.

FIGS. 3 and 4 illustrate a visual indicator according to certain embodiments. FIGS. 3 and 4 illustrate, on the left, eye 102 which includes retina 103. Surgical instrument 146 (here, a vitrectomy probe) and light source 145 are inserted into a posterior region of eye 102. FIGS. 3 and 4 further illustrate, on the right, corresponding microscope images displayed to a system operator via eyepieces 104 (with input from real-time data projection unit 116) and/or display 132. The microscope images show fundus 105, surgical instrument 146 (which may include marker 147, not shown), and indicator 300 generated by tracking unit 144. As shown in the embodiments of FIGS. 3 and 4, indicator 300 appears as an overlay superimposed at distal tip 149 of surgical instrument 146. Indicator 300 may appear as an overlay superimposed entirely on distal tip 149 (such that no part of the indicator is outside a boundary formed by the edged of distal tip 149), so as not to block a surgeon's view of fundus 105. According to certain embodiments, indicator 300 may alternatively appear as an indicator partially covering distal tip 149, or near distal tip 149 without covering it. As surgical instrument 146 moves within eye 102, tracking unit 144 tracks distal tip 149 and maintains the indicator 300 as an overlay on or near distal tip 149. Additionally, a characteristic of indicator 300 is shown to be modified incrementally, and (although not to scale) proportional to the change in distance between distal tip 149 and retina 103.

In the embodiments of FIG. 3, indicator 300 becomes as larger distal tip 149 approaches retina 103. In FIG. 3A, the distal tip 149 of surgical instrument 146 is separated by a relatively large distance from retina 103. Accordingly, tracking unit 144 generates for display a relatively large indicator 300 (here, a triangle) that overlays distal tip 149 in the microscope image shown on the right. In FIG. 3B, the distance between distal tip 149 and retina 103 has decreased, and in FIG. 3C it has decreased even further. As distal tip 149 approaches retina 103, tracking unit 144 decreases the size of indicator 300 to convey that distal tip 149 is getting closer to retina 103 (and/or further from the imaging unit or system operator). In this manner, the size of visual indicator 300 may be increased or decreased in proportion to the change in distance between distal tip 149 and retina 103. Because tracking unit 144 continuously (or frequently) adjusts the size of visual indicator 300 in small increments, it may provide a surgeon with an intuitive, real-time indication of the depth of distal tip 149 and its distance from retina 103. Thus, in this example, a characteristic of the visual indicator (in this example, size) is modified in response to a change in distance between distal tip 149 and retina 103. This example further illustrates how indicator 300 may be modified to track the movement of distal tip 149 within the microscope images. That is, indicator 300 is maintained as an overlay even as distal tip 149 moves within the microscope image.

FIG. 4 illustrates how additional characteristics and indicators may be used in certain embodiments. As with FIG. 3, FIG. 4 shows that indicator 300 (here, a circle) becomes relatively smaller as distal tip 149 approaches retina 103 in FIGS. 4B and 4C, and indicator 300 is maintained as an overlay even as distal tip 149 moves within the microscope images on the right side of the figure.

In addition, indicator 300 of FIG. 4 changes transparency according to the distance calculated by tracking unit 144. In FIG. 4A, where distal tip 149 of surgical instrument 146 is a relatively large distance from retina 103, indicator 300 appears as nearly transparent. In FIG. 4B, as the distance decreases, indicator 300 is semi-transparent. And in FIG. 4C, indicator 300 becomes opaque and begins flashing when the distance drops below a predetermined threshold distance (e.g., 0.5 mm). Indicator 300 may additionally become brighter (or more intense) as the distance decreases, such that it transitions from a low brightness in FIG. 4A to medium brightness in FIG. 4B to a maximum brightness in FIG. 4C. Accordingly, various characteristics of visual indicator 300 may be altered in proportion to the change in distance between distal tip 149 and retina 103 to provide an intuitive indication of the depth of distal tip 149.

The microscope images of FIG. 4 also depict a second indicator 302, which is a numerical value of the determined distance between distal tip 149 and retina 103 (here, in millimeters). Secondary indicator 302 is shown here as an overlay positioned near distal tip 149, but it may be positioned elsewhere within the microscope view in other embodiments.

FIG. 4 additionally depicts a third indicator 304, which comprises a colored ring about the outer edge of the microscope view. In this example, indicator 304 changes color according to the determined distance, transitioning from green to yellow and red in FIGS. 4A, 4B, and 4C, respectively. Indicator 304 may change characteristics in the same manner as indicator 300 to indicate proximity and/or distance (e.g., change brightness, transparency, flash rate, etc.).

It should be understood that the examples discussed above are non-limiting, and the present disclosure contemplates that indicator 300 may take any suitable form and have any suitable characteristics to indicate the position, orientation, and depth of distal tip 149, or its distance from or proximity to the retina.

Figure 5:
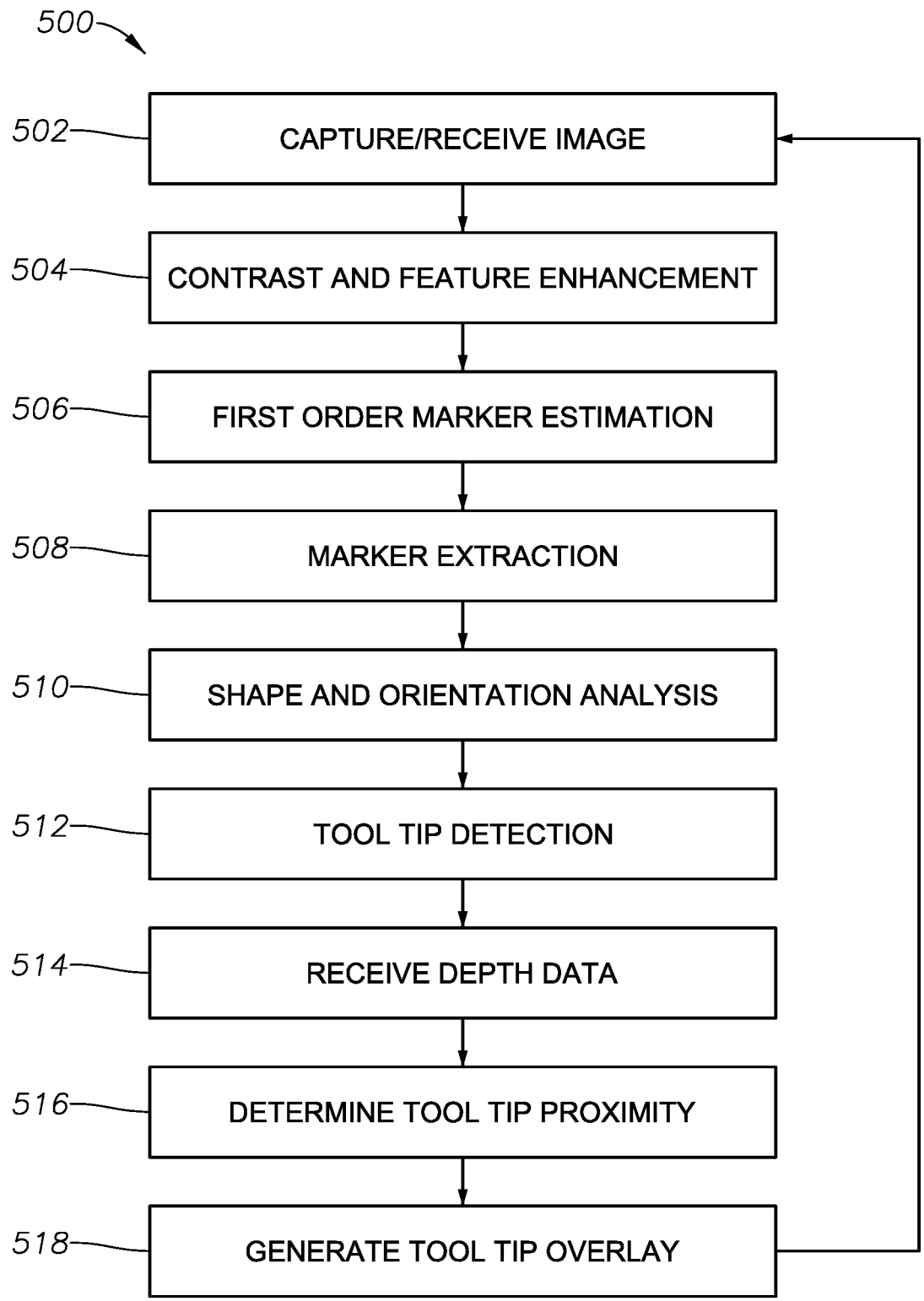
FIG. 5 is a flow chart illustrating a method for tracking and indicating the location of a surgical instrument inserted in an eye and its proximity to eye tissue, according to certain embodiments.

FIG. 5 is a flow chart illustrating a method 500 for determining, tracking and indicating the depth and location of surgical instrument 146 in accordance with certain embodiments. Certain examples of tracking unit 144 include a processor configured to (or may store software in memory that, when executed by a processor, is operable to) perform the steps of method 500.

At step 502, tracking unit 144 receives an image of the fundus. For example, tracking unit 144 may receive one or more photographs or video frames captured by imaging unit 142.

At step 504, tracking unit 144 may perform contrast and feature enhancement processing on received image. For example, tracking unit 144 may receive an image in Red-Green-Blue (RGB) format. Tracking unit 144 may convert the RGB format image into a Hue-Saturation-Value (HSV) space.

At step 506, tracking unit 144 may determine a first-order estimation mask of a marker (e.g., marker 147) in the image. For example, based on a predetermined color of marker 147, tracking unit 144 may apply criteria to the hue and saturation channels of the HSV image to separate marker 147 from a background, in order to bring out and estimate the image of marker 147.

At step 508, tracking unit 144 may extract the image of marker 147 from a fundus image and identify the position of the marker. For example, tracking unit 144 may utilize a blob detection process to detect a boundary of marker 147 in image 148 by searching for regions of approximately constant properties in the image frame. Thus, tracking unit 144 may find the boundary of marker 147 and extract it from the image frame to determine its position in an image.

At step 510, tracking unit 144 may analyze the shape and orientation of marker 147 extracted from an image frame and may determine the orientation of the marker based on a predetermined pattern or color (e.g., a location and direction of stripes). For example, if marker 147 has stripes, tracking unit 144 may determine the orientation of marker 147 based on the orientation and direction of the stripes.

At step 512, tracking unit 144 may determine the position and orientation of distal tip 149 of surgical instrument 146 within an image frame. In particular embodiments, tracking unit 144 may determine the location and orientation of distal tip 149 in an image based on the location and orientation determinations for marker 147 (described in preceding steps). To facilitate such determinations, marker 147 may be positioned at a predetermined distance from distal tip 149 and may have a pattern that indicates a pointing direction of surgical instrument 146 (e.g., a strip, stripes, or an arrow). Thus, based on the position and pattern of marker 147, tracking unit 144 may determine the position of distal tip 149 and the pointing direction or orientation of surgical instrument 146.

At step 514, tracking unit 144 receives image data from an imaging system that generates a depth-resolved image of eye 102. Such images may include surgical instrument 146 (if obtained by an imaging probe external to the instrument), or may be obtained using surgical instrument 146 itself (e.g., via one or more optical fibers extending to the tip of instrument 146). In certain embodiments, tracking unit 144 receives image data from OCT system 114. In other embodiments, tracking unit 144 may receive image data from an alternative system that provides depth-resolved or three-dimensional image data, such as an ultrasound imaging system, a multispectral imaging system, a computerized axial tomography (CAT) scan system, a magnetic resonance imaging (MRI) system, a positron emission tomography (PET) imaging system, or other imaging system. Tracking unit 144 may analyze the received image data to identify the depth of, and distance or proximity between, distal tip 149 and the retina of eye 102.

At step 516, tracking unit 144 analyzes the received image data to determine the depth and proximity of distal tip 149 and the retina of eye 102. Tracking unit 144 may process an image received at step 514 (or data related to or extracted from the image) to calculate a distance between a part of surgical instrument 146 (e.g., distal tip 149) and tissue in eye 102 (e.g., the retina). For example, tracking unit 144 may register depth image data and identify the coordinates of identified features in the depth-resolved image. Such coordinates may be digitized using computer vision or machine vision algorithms, such as edge or blob detection, and may be used to calculate the distance between features within the image.

In certain embodiments, tracking unit 144 may determine the distance or proximity between the retina of eye 102 and the distal tip 149 based on characteristics of the received depth image. Tracking unit 144 may determine the distance or proximity between the retina of eye 102 and the distal tip 149 based on the degree of separation between them in the image. In certain embodiments, tracking unit 144 may determine distance or proximity based on the number of pixels separating retina of eye 102 and the distal tip 149 in an OCT image, which may have a fixed z-depth resolution. In certain embodiments, tracking unit 144 may determine the distance or proximity based on the pixels between the edge of the image (or other feature corresponding to the distal tip 149) and a retina of eye 102 depicted in an OCT image.

At step 518, tracking unit 144 generates an indicator for display as an overlay on distal tip 149 within a microscope image. Certain embodiments of tracking unit 144 may generate one or more visual indicators based on the determined location, depth, and orientation of surgical instrument 146, and overlay the indicator into a microscope image for surgical guidance. For example, based on the determinations of steps 512 and 516, tracking unit 144 may generate an indicator for display by real-time data projection unit 116 or display 132 to alert a system operator of the proximity of distal tip 149 to particular eye tissue, such as the retina. As described above, a characteristic of the indicator may indicate the proximity of or distance between distal tip 149 and the retina of eye 102. Tracking unit 144 may apply the indicator as an overlay at the determined location of distal tip 149 in image 148. In this manner, the indicator can alert the system operator as distal tip 149 approaches the retina of eye 102.

Tracking unit 144 may perform method 500 for multiple fundus images 148 received from imaging unit 142 to track the position and orientation of distal tip 149, and the distance between distal tip 149 and the retina of eye 102, in real time. Thus, real-time data projection unit 116 and display 132 may project or display the generated indicator(s) as an overlay in a real-time video of the fundus to track the position and movement of distal tip 149, as well as its proximity to the retina of eye 102.

Figure 6:
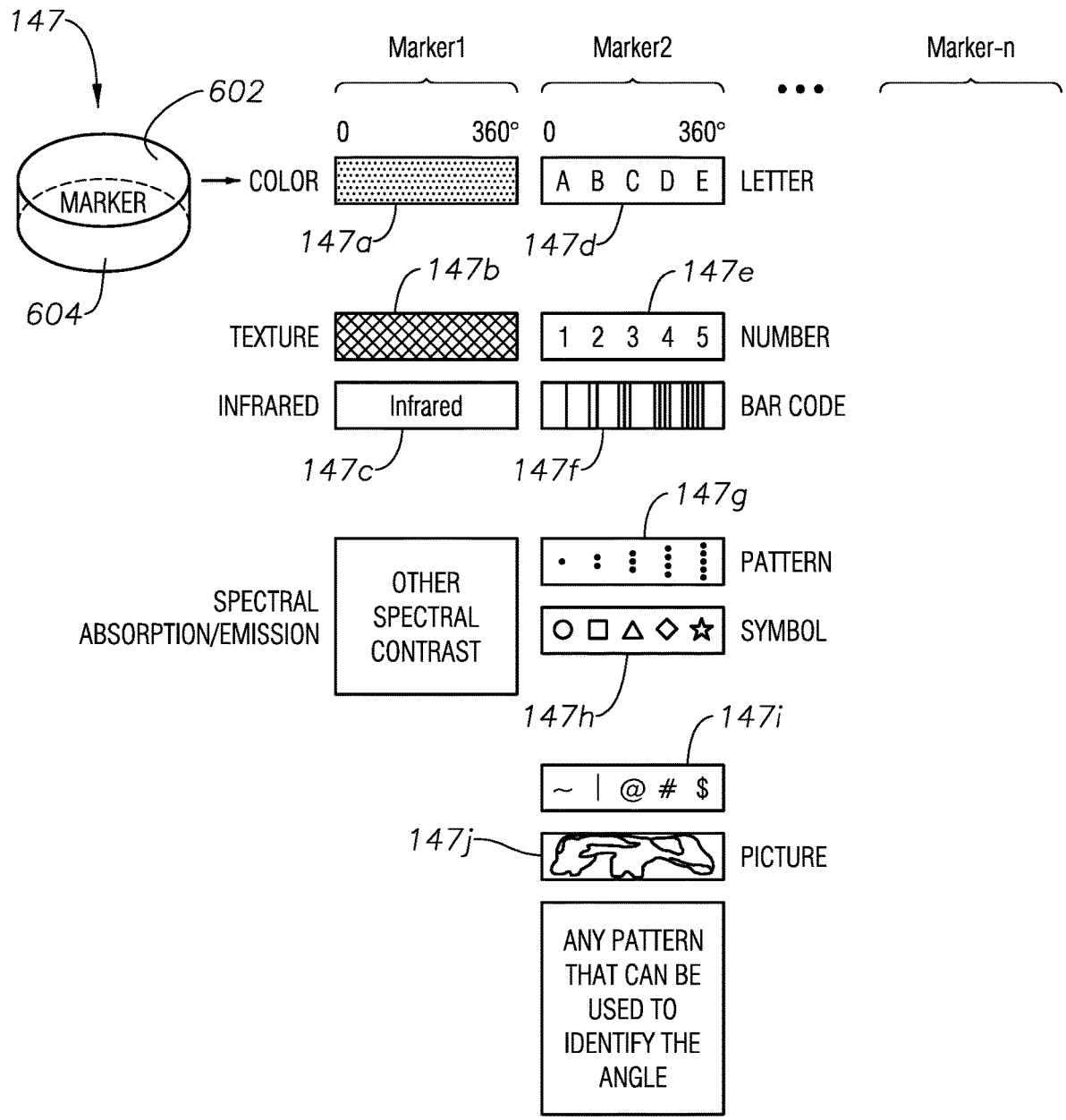
FIG. 6 illustrates various types of markers for a surgical instrument, according to certain embodiments.

FIG. 6 illustrates various examples of marker 147. Marker 147 may have a ring, ribbon shape configured to wrap around the distal portion 143 of surgical instrument 146. Marker 147 may have an inner surface 602 and an outer surface 604. Inner surface 602 may have adhesives and may be configured to adhere or bond to an exterior surface of surgical instrument 146. The exterior surface of distal portion 143 may have a circumferential groove configured to accommodate the ring, ribbon shape marker 147. Thus, marker 147 may fit securely in the circumferential groove. Outer surface 604 may have colors or patterns configured to distinguished marker 147 from other elements in a fundus image.

One or more markers 147 may be used for surgical instrument 146. Marker 147 may be formed of bio-compatible and/or synthetic materials, such as sterile plastic. In some embodiments, marker 147 may be a layer of paint inscribed on an exterior surface of the distal portion 143 of surgical instrument 146. Markers 147 may overlap one another or be separate. Markers 147 may have one or more high-contrast colors, such as green, which does not appear in a typical fundus image. Thus, a green marker 147 may be distinguished from other elements in the fundus image. Markers 147 may have various color, texture, or special contrast characteristics. Markers 147 may include patterns that may identify an orientation and angle of instrument 146. For example, as shown in FIG. 6, marker 147a may have a solid high-contrast color. When the ring, ribbon shape marker 147a is cut open, the marker 147a may be a ribbon in solid color. In another example, marker 147b may have a texture pattern that may distinguish the marker 147b from the background fundus image. Exemplary marker 147c may include an infrared color configured to reflect or emit infrared light. Markers 114 with various spectral absorption/emission also may be used.

Markers 114 may include letters, numbers, bar codes, pattern, symbols, or pictures. Exemplary marker 147d may include letters. As shown in FIG. 6, assuming that marker 147d wraps 360 degrees around the distal portion 143 of the instrument 146, a letter "A" may be positioned near the zero degree position and the letter "E" may be positioned near the 360 degree position. Letters 15 "B," "C," and "D" may be positioned in between "A" and "E" at respective positions. Thus, based on the orientation of the letters, the rotational position of marker 147d and indirectly the rotational position of surgical instrument 146 may be determined. Exemplary marker 147e may include numbers "1" to "5." Similarly, the numbers may indicate a rotational position of surgical instrument 146. Further, the orientation of the letters or number also may indicate a tilting angle of the surgical instrument 146. For example, the numbers or letters may be orientated relatively to the distal tip 149 such that the bottoms of the numbers or letter face toward the distal tip 149. Thus, based on the orientation of the numbers or letters, the tilting angle of the distal tip 149 may be determined.

Exemplary marker 147f may include barcodes or stripes. The direction of the stripes may indicate a tilting angle of the surgical instrument 146. Further, the number of stripes may vary to indicate a rotational position of marker 147f and indirectly, the rotational position of the surgical instrument 146. Marker 147g has various dot patterns. The number of dots may indicate the rotational position of marker 147f and the alignment of the dots may indicate a tilting angle of the marker 147f Other symbols also may be used on markers 114. For example, various symbols, such as shapes or non-character symbols may be used at different rotational positions of markers 114h and 114i to indicate rotational positions. In addition, a picture may be used to indicate rotational and tilt positions of marker 114j. Other patterns or symbols that may indicate an orientation and position of the surgical instrument 146 also may be used on the markers 114.

Figure 7A:
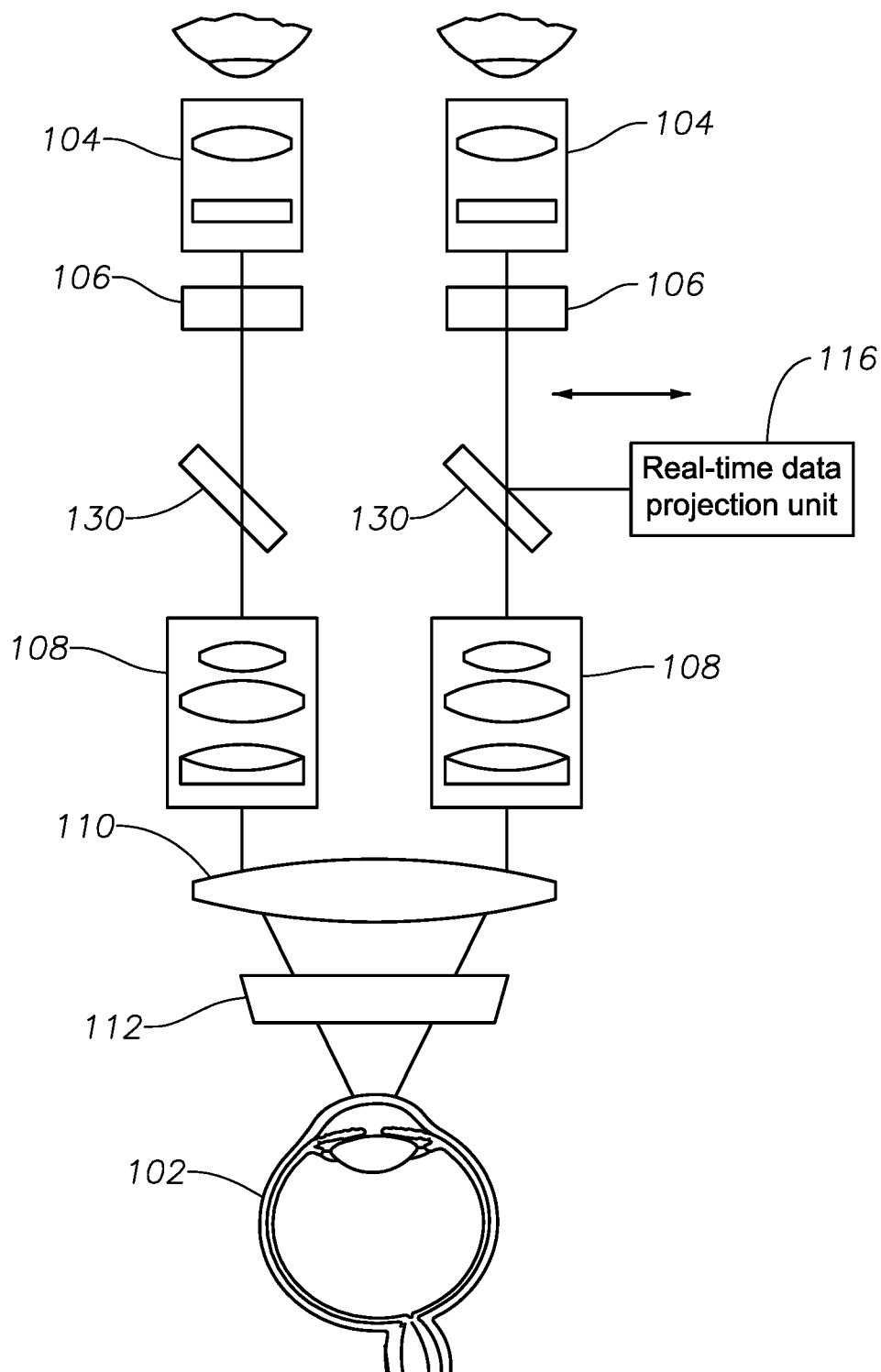
FIGS. 7A-7B illustrate example ophthalmic surgical visualization systems that include switchable single-channel data injection, according to certain embodiments.
Figure 7B:
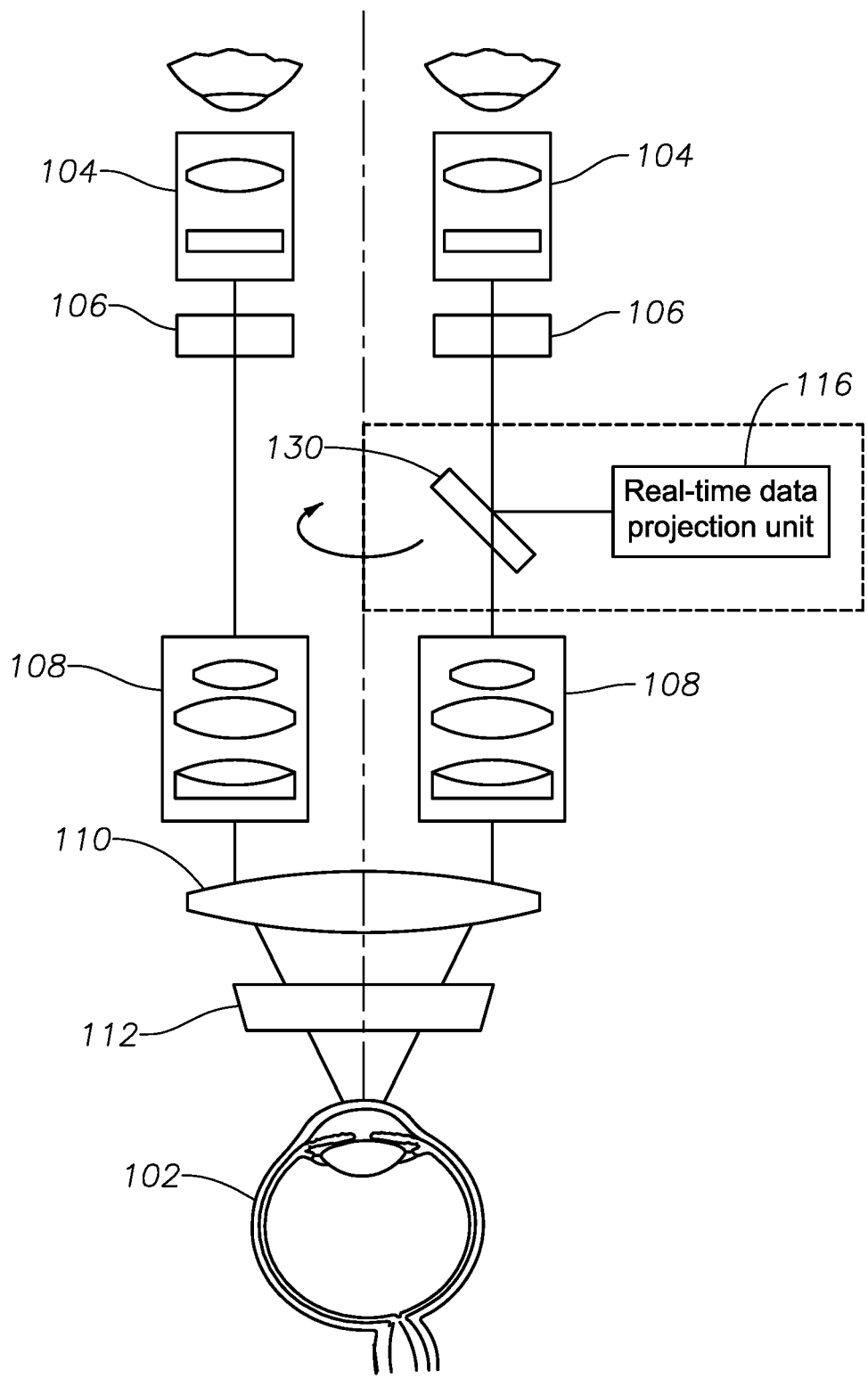

FIGS. 7A-7B illustrate embodiments of ophthalmic surgical microscope 100 having switchable single channel data injection, according to certain embodiments of the present disclosure. Although FIGS. 7A-7B do not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment depicted in FIGS. 7A-7B, ophthalmic surgical microscope 100 includes a real-time data projection unit 116 capable of single channel data injection (i.e., the images injected by real-time data projection unit 116 are viewable through only one of the two eyepieces 104, as in FIG. 1). However, unlike the embodiment depicted in FIG. 1, the embodiment depicted in FIGS. 7A-7B provides the ability to change which channel (i.e., eyepiece 104) onto which the data is injected. More particularly, FIG. 7A depicts an embodiment in which one or both of real-time data projection unit 116 and beam splitter 130 can translate side to side in order to change the channel onto which data is injected while FIG. 7B depicts an embodiment in which the assembly of real-time data projection unit 116 and beam splitter 130 rotatable about a midpoint of surgical microscope 100 in order to change the channel onto which data is injected. As a result, a surgeon may be provided the flexibility to select which eye is used to view the injected data.

Figure 8:
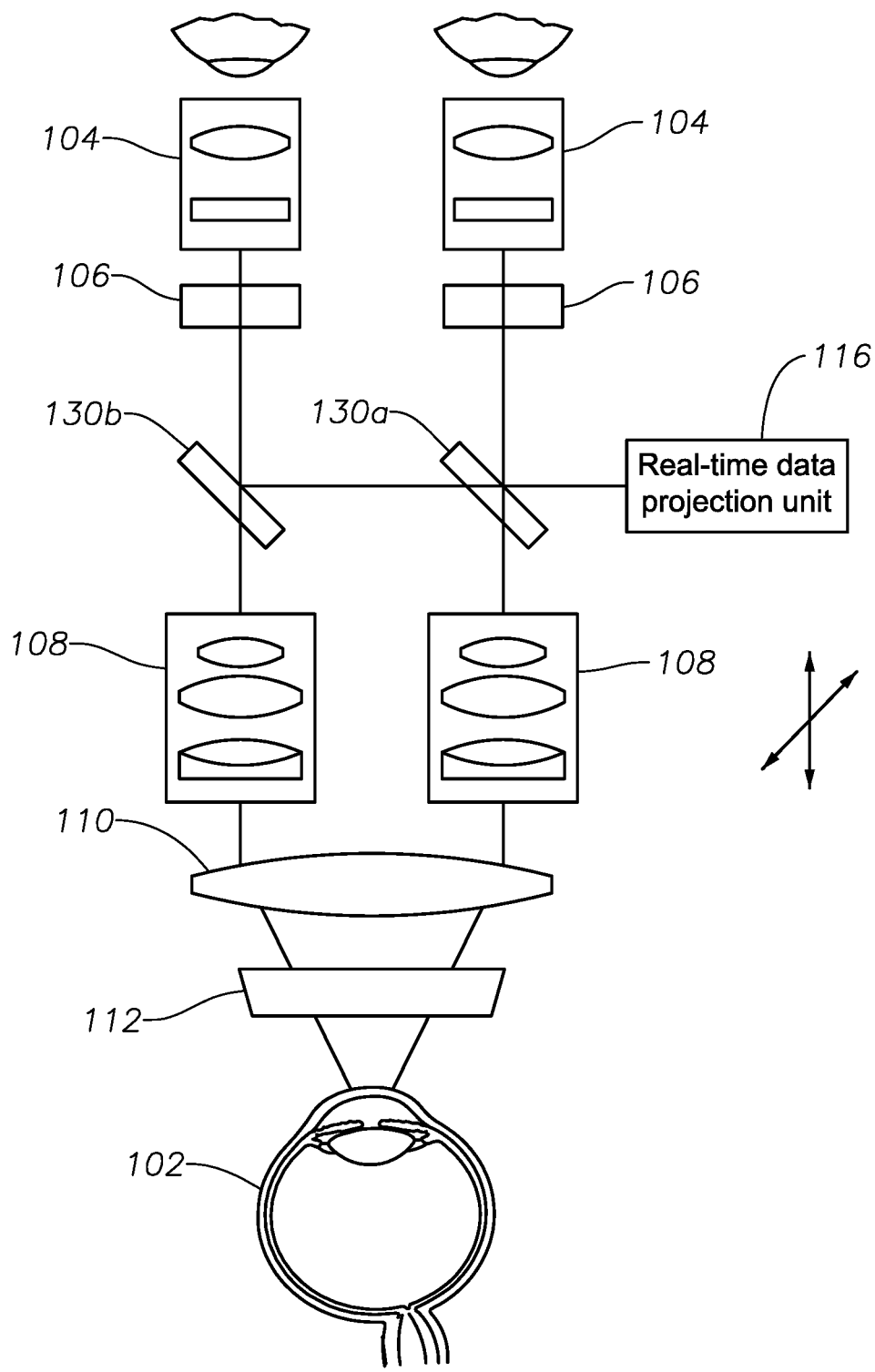
FIG. 8 illustrates an example ophthalmic surgical visualization system that includes two-channel data injection, according to certain embodiments.

FIG. 8 illustrates an embodiment of ophthalmic surgical microscope 100 having two-channel data injection, according to certain embodiments of the present disclosure. Although FIG. 8 does not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment depicted in FIG. 8, surgical microscope 100 include a single real-time data projection unit 116 and two beam splitters 130 (130a and 130b) each associated with a corresponding channel of the microscope. Beam splitters 130a and 130b may be configured such that the data projected by real-time data projection unit 116 is duplicated and viewable via both of the eyepieces 104. Reflectivities of the beam splitters 130a and 130b may be selected such that the brightness of the image viewable through each eyepiece 104 is the same. Moreover, beam splitters may be movable in order to change the shifted within the surgeon's field of view. Alternatively, movement within the surgeon's field of view may be achieved by placing a beam deflection device (e.g., an acoustical optical deflector) in the optical path of the image projected by real-time data projection unit 116.

Figure 9:
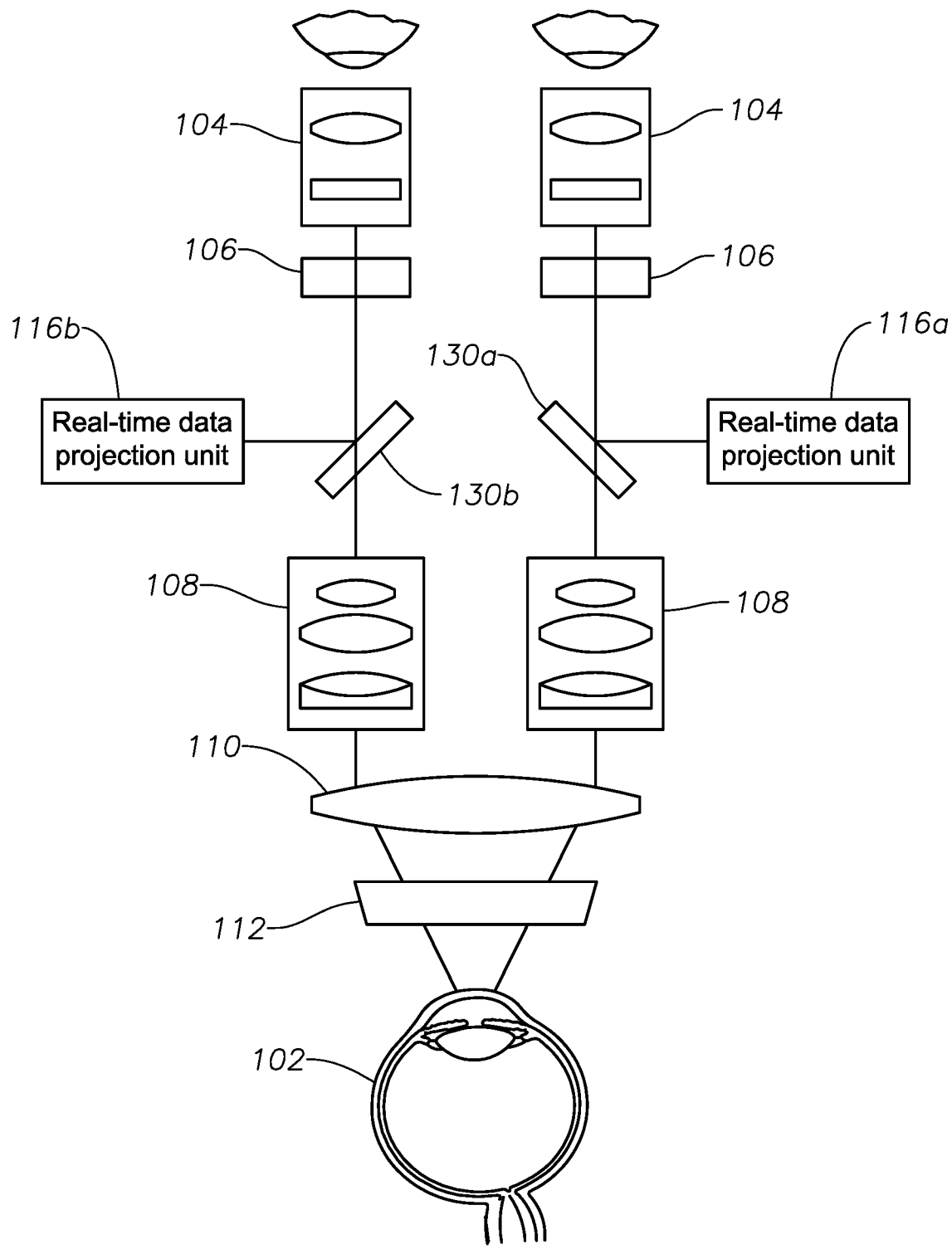
FIG. 9 illustrates another example ophthalmic surgical visualization system that includes two-channel data injection, according to certain embodiments.

FIG. 9 illustrates an alternative embodiment of ophthalmic surgical microscope 100 having two-channel data injection, according to certain embodiments of the present disclosure. Although FIG. 9 does not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiment of FIG. 9, two real-time data projection units 116 are included (116a and 116b). Each real-time data projection unit projects an image, which is coupled into the optical path of the surgical microscope by a corresponding beam splitter 130. Because each real-time data projection unit can inject a unique image, the embodiment of FIG. 4 may facilitate 3-D perception. More particularly, each real-time data projection unit 116 may project the same image but with slightly different perspectives so as to provide 3-D perception when viewed through eyepieces 104.

Figure 10A:
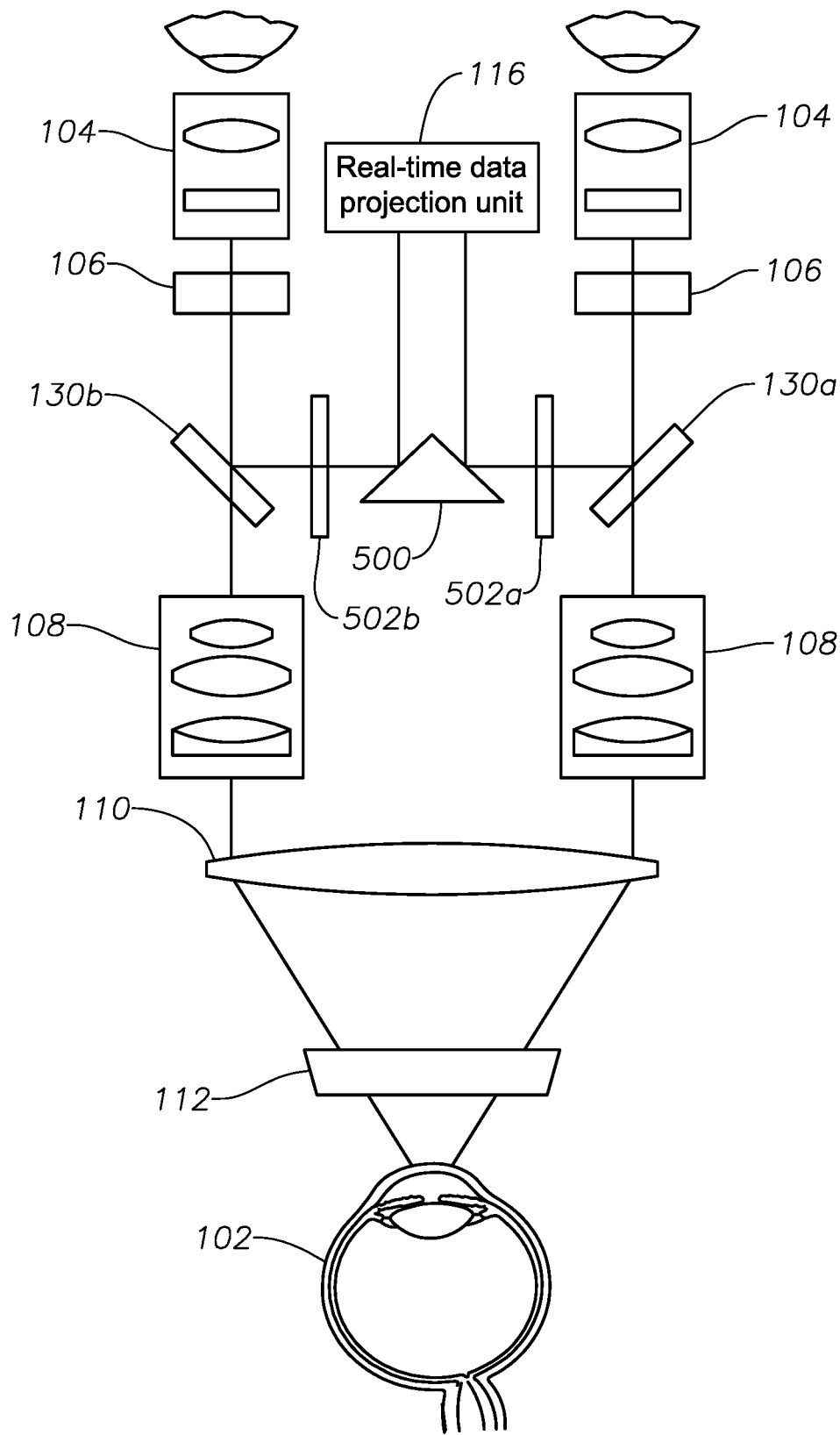
FIGS. 10A-10C illustrate example ophthalmic surgical visualization systems that include two-channel data injection with 3-D perception, according to certain embodiments.
Figure 10B:
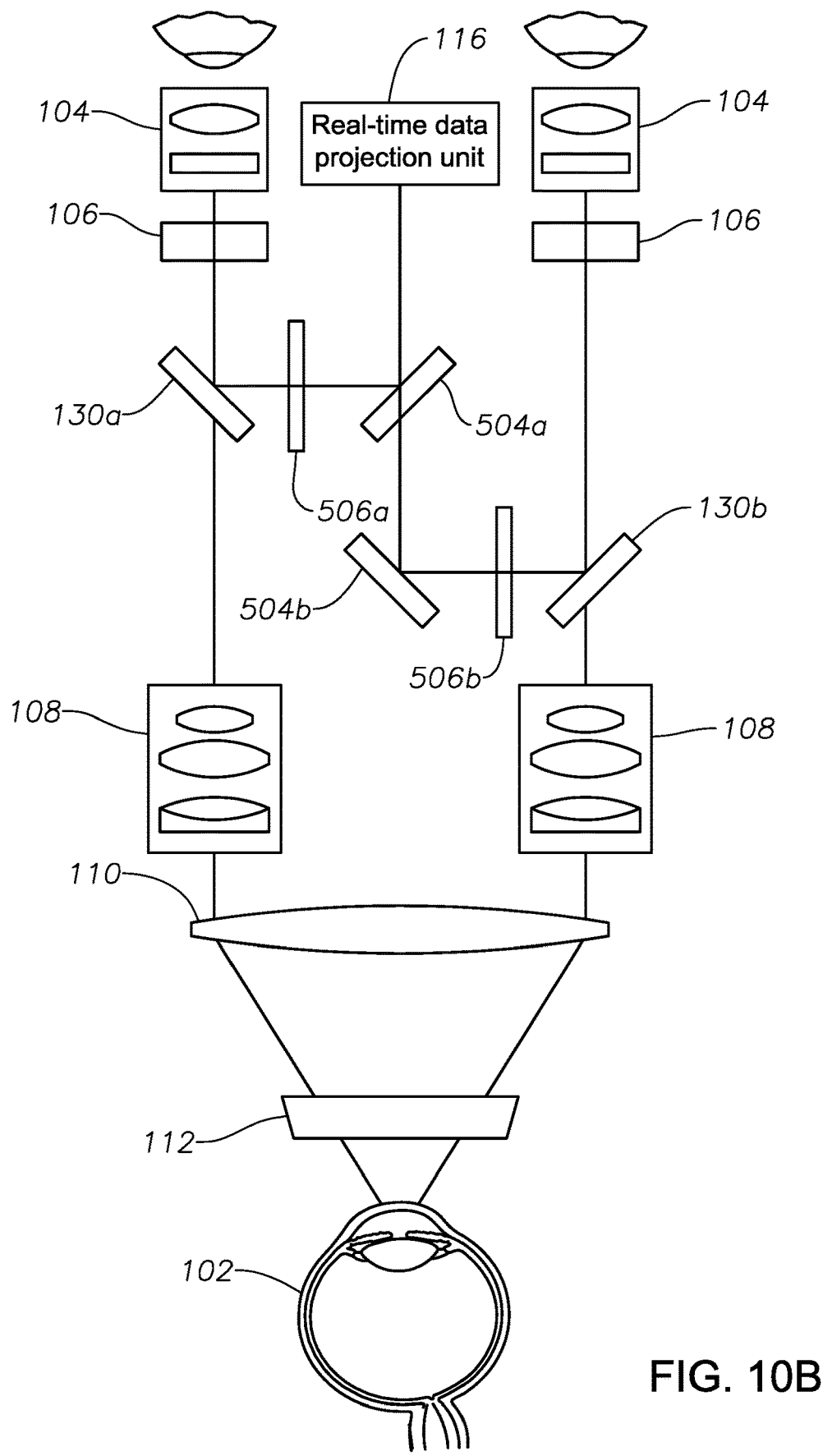
Figure 10C:
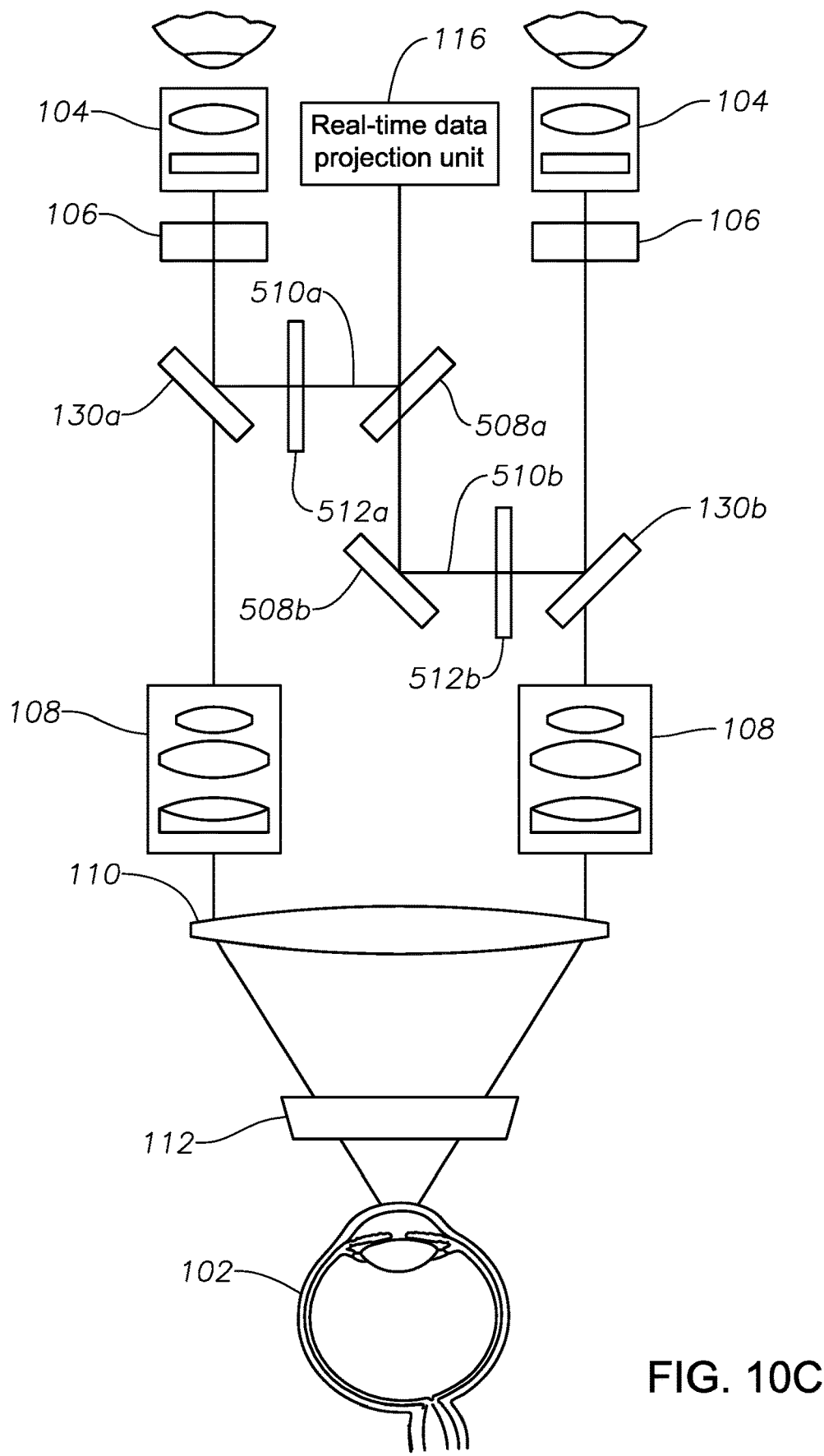

FIGS. 10A-10C illustrate embodiments of ophthalmic surgical microscope 100 having two-channel data injection with 3-D perception, according to certain embodiments of the present disclosure. Although FIGS. 10A-10C do not depict certain components of ophthalmic surgical microscope 100 as depicted in FIG. 1 for the sake of simplicity, the present disclosure contemplates that those components be included and that they function in substantially the same manner as described above with regard to FIG. 1.

In the embodiments depicted in FIGS. 10A-10C, 3-D perception is facilitated using one real-time data projection unit 116 rather than two (as in the embodiment described above with regard to FIG. 4). In the embodiment depicted in FIG. 10A, a single real-time data projection unit 116 projects side-by-side images, which may be slightly different to provide 3-D perception (as described above). The projected side-by-side images may be split by a beam splitter 500 and projected into each eyepiece 104 by beam splitter 130a and 130b. In certain embodiments, filters 502a and 502b may also be placed in the optical path of the projected images to further facilitate 3-D perception.

In the embodiment depicted in FIG. 10B, real-time data projection unit 116 may project a color-coded image (such as a red and cyan coded image in anaglyph), and that color coded image may pass through beam splitters 504a and 504b to be directed toward the two channels of surgical microscope 100. Filters 506a and 506b may be placed in the optical path of the image for each channel to separate the color-coded information. For example, filter 506a (such as a red filter) may be inserted into the left channel and filter 506b (such as a cyan filter) may be added to the right channel to separate the red/cyan information in the projected image. By properly calibrating the projected image, 3-D perception may be provided without the need for the surgeon to wear extra glasses or optical devices.

In the embodiment depicted in FIG. 10C, real-time data display unit 116 may be a polarized display/projector (such as a polarization modulated projector) and may project a polarization encoded image. The projected polarization encoded image may pass through polarizing beam splitters 508a and 508b to be divided between the two channels. For example, a p polarized image may be split into one eye (designated as 510a) while an s polarized image will be split into the other eye (designated as 510b). Additionally or alternatively, by inserting wave plates 512a and 512b into the two channels, a left hand circular polarized image may be split into one eye while a right hand circular polarized image may be split into the other eye. By properly calibrating the projected image, 3-D perception may be provided without the need for the surgeon to wear extra glasses or optical devices.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic surgical system, comprising:
an imaging unit configured to generate a fundus image of an eye;
a depth imaging system configured to generate a depth-resolved image of the eye;
a tracking system for tracking the location, depth, and movement of a surgical instrument, the tracking system communicatively coupled to the imaging unit and depth imaging system, the tracking system comprising a processor and memory configured to:
analyze the fundus image generated by the imaging unit to determine a location of a distal tip of the surgical instrument in the fundus image;
analyze the depth-resolved image generated by the depth imaging system to determine a distance between the distal tip of the surgical instrument and a retina of the eye in the depth direction;
generate a visual indicator to overlay the distal tip of the surgical instrument within a portion of the fundus image, the visual indicator indicating the determined distance between the distal tip and the retina in the depth direction, the visual indicator remaining on the distal tip as the surgical instrument moves;
modify the visual indicator to track a change in the location of the distal tip within the fundus image in real-time; and
modify a brightness or a transparency of the visual indicator to indicate a change in the distance between the distal tip of the surgical instrument and the retina in the depth direction in real-time; wherein the brightness increases or the transparency decreases as the distance between the distal tip of the instrument and the retina decreases.

2. The ophthalmic surgical system of claim 1, wherein:
the processor and memory of the tracking system are further configured to determine the distance between the distal tip of the surgical instrument and the retina of the eye in the depth direction based on an analysis of image pixels in the depth-resolved image.

3. The ophthalmic surgical system of claim 1, wherein: the depth-imaging system is configured to generate the depth-resolved image of the eye based on signals received by an imaging probe integrated with the surgical instrument.

4. The ophthalmic surgical system of claim 1, wherein the processor and memory of the tracking system are configured to modify the visual indicator to indicate the change in the distance between the distal tip of the surgical instrument and the retina in the depth direction by increasing or decreasing the size of the visual indicator in proportion to the change in distance between the distal tip of the surgical instrument and the retina in the depth direction.

5. The ophthalmic surgical system of claim 1, wherein the processor and memory of the tracking system are configured to modify the visual indicator to indicate the change in the distance between the distal tip of the surgical instrument and the retina in the depth direction by modifying a color of the visual indicator.

6. The ophthalmic surgical system of claim 1, wherein:
the depth imaging system is an Optical Coherence Tomography (OCT) system configured to generate an OCT image of the eye, the OCT system comprising:
an OCT light source operable to generate an OCT imaging beam; and
a beam scanner operable to direct the OCT imaging beam; and
the tracking system is configured to analyze the OCT image to determine the distance between the distal tip of the surgical instrument and the retina of the eye in the depth direction.

7. The ophthalmic surgical system of claim 6, wherein the processor and memory of the tracking system are further configured to cause the beam scanner to direct the OCT imaging beam to a particular region of the eye that includes the distal tip of the surgical instrument, based on the determined location of the distal tip of the surgical instrument within the fundus image.

8. The ophthalmic surgical system of claim 6, wherein the surgical instrument includes a first optical fiber configured to transmit the OCT imaging beam, and a second optical fiber configured to transmit light reflected by the eye.

9. The ophthalmic surgical system of claim 1, wherein the processor and memory of the tracking system are configured to determine the location of the distal tip of the surgical instrument in the fundus image by:
generating an enhanced image of the fundus image;
estimating a marker image within the enhanced image;
extracting the marker image from the enhanced image; and
determining a location of the marker from the image of the marker.

10. The ophthalmic surgical system of claim 1, wherein the visual indicator and fundus image are displayed in an eyepiece or on a heads-up screen.

11. The ophthalmic surgical system of claim 1, wherein the visual indicator is configurable by a user.

12. The ophthalmic surgical system of claim 1, wherein the imaging unit comprises at least one of a surgical microscope, a 2-dimensional camera, a line-scan camera, and a single detector as used in a confocal scanning ophthalmoscope.

13. A method, comprising:
generating a fundus image of an eye;
generating a depth-resolved image of the eye;
analyzing the fundus image to determine a location of a distal tip of a surgical instrument in the fundus image;
analyzing the depth-resolved image to determine a distance between the distal tip of the surgical instrument and a retina of the eye in the depth direction;
generating a visual indicator to overlay the distal tip of the surgical instrument within the fundus image, the visual indicator indicating the determined distance between the distal tip and the retina in the depth direction, the visual indicator remaining on the distal tip as the surgical instrument moves;
modifying the visual indicator to track a change in the location of the distal tip within the fundus image in real-time; and
modifying a brightness or a transparency of the visual indicator to indicate a change in the distance between the distal tip of the surgical instrument and the retina in the depth direction in real-time; wherein the brightness increases or the transparency decreases as the distance between the distal tip of the instrument and the retina decreases.

14. The method of claim 13, wherein modifying the visual indicator to indicate a change in the distance between the distal tip of the surgical instrument and the retina in the depth direction in real-time comprises increasing or decreasing the size of the visual indicator in proportion to the change in distance between the distal tip of the surgical instrument and the retina in the depth direction.

15. The method claim 13, wherein modifying the visual indicator to indicate a change in the distance between the distal tip of the surgical instrument and the retina in real-time comprises modifying a color of the visual indicator.

16. The method claim 13, further comprising: directing an imaging beam of an imaging system to a particular region of the eye that includes the distal tip of the surgical instrument, based on the determined location of the distal tip of the surgical instrument within the fundus image.

17. The method claim 13, wherein analyzing the fundus image to determine a location of the distal tip of a surgical instrument in the fundus image comprises:
generating an enhanced image of the fundus image;
estimating a marker image within the enhanced image;
extracting the marker image from the enhanced image; and
determining a location of the marker from the image of the marker.

18. The method claim 13, further comprising: displaying the visual indicator in an eyepiece or on a heads-up screen.

19. The method claim 13, further comprising: receiving user input related to a type of visual indicator.

* * * * *